(12) United States Patent
Jain et al.

(10) Patent No.: US 9,474,805 B2
(45) Date of Patent: *Oct. 25, 2016

(54) DERIVATISATION OF GRANULOCYTE COLONY-STIMULATING FACTOR

(71) Applicant: Lipoxen Technologies Limited, London (GB)

(72) Inventors: Sanjay Jain, London (GB); Peter Laing, London (GB); Gregory Gregoriadis, London (GB)

(73) Assignee: Lipoxen Technologies Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/720,700

(22) Filed: May 22, 2015

(65) Prior Publication Data

US 2015/0252090 A1 Sep. 10, 2015

Related U.S. Application Data

(63) Continuation of application No. 13/646,584, filed on Oct. 5, 2012, now Pat. No. 9,040,478, which is a continuation of application No. 12/375,006, filed as application No. PCT/GB2007/002816 on Jul. 25, 2007, now Pat. No. 8,299,015.

(30) Foreign Application Priority Data

Jul. 25, 2006 (EP) .................................... 06117830

(51) Int. Cl.
| | | |
|---|---|---|
| *A01N 37/18* | (2006.01) | |
| *A61K 38/00* | (2006.01) | |
| *C07K 1/00* | (2006.01) | |
| *A61K 38/16* | (2006.01) | |
| *C07K 14/00* | (2006.01) | |
| *A61K 47/48* | (2006.01) | |
| *A61K 38/18* | (2006.01) | |
| *C07K 14/535* | (2006.01) | |
| *C07K 14/52* | (2006.01) | |
| *C07K 14/505* | (2006.01) | |
| *C07K 14/575* | (2006.01) | |
| *A61K 38/46* | (2006.01) | |
| *A61K 38/19* | (2006.01) | |

(52) U.S. Cl.
CPC ....... *A61K 47/4823* (2013.01); *A61K 38/1816* (2013.01); *A61K 38/193* (2013.01); *A61K 38/465* (2013.01); *C07K 14/505* (2013.01); *C07K 14/52* (2013.01); *C07K 14/535* (2013.01); *C07K 14/575* (2013.01); *A61K 38/00* (2013.01); *C12Y 301/21001* (2013.01)

(58) Field of Classification Search
None
See application file for complete search history.

(56) References Cited

U.S. PATENT DOCUMENTS

| | | | |
|---|---|---|---|
| 5,846,951 A | 12/1998 | Gregoriadis | |
| 6,956,027 B2 | 10/2005 | Kinstler | |
| 8,299,015 B2 | 10/2012 | Jain et al. | |
| 2007/0014759 A1 | 1/2007 | DeFrees et al. | |
| 2007/0254836 A1* | 11/2007 | Defrees ............... | A61K 38/193 514/54 |

FOREIGN PATENT DOCUMENTS

| | | |
|---|---|---|
| WO | 9222331 A1 | 12/1992 |
| WO | 9611953 A1 | 4/1996 |
| WO | 0187922 A2 | 11/2001 |
| WO | 03031464 A1 | 4/2003 |
| WO | 03055526 A2 | 7/2003 |
| WO | 2005003149 A1 | 1/2005 |
| WO | 2005014050 A1 | 2/2005 |
| WO | 2005016973 A1 | 2/2005 |
| WO | 2005016974 A1 | 2/2005 |
| WO | 2005055946 A2 | 6/2005 |
| WO | 2006016168 A2 | 2/2006 |
| WO | 2006074467 A2 | 7/2006 |
| WO | 2006074467 A3 | 7/2006 |
| WO | 2006090119 A1 | 8/2006 |

OTHER PUBLICATIONS

Kolchanov, 1988, Journal of Molecular Evolution, vol. 27, pp. 154-162.*
Pasquo, 2012, PLoS ONE, vol. 7, Issue 2, e32555.*
Bork, 2000, Genome Research 10:398-400.*
Bork et al., 1996, Trends in Genetics 12:425-427.*
Nissen et al. Drug Invest. (1994), vol. 7(6), p. 346-352.*
Gregoriadis et al., Int. J. Pharm. 2005, V. 300, p. 125-130.
Jain et al., BBA General Subjects, 2003, V. 1622, p. 42-49.
Defrees et al., "GlycoPEGylation of recombinant therapeutic proteins produced in *E. coli*.", Glycobiology, Jun. 22, 2006, V. 16, No. 9, pp. 833-843.
Fernandes and Gregoriadis, BBA (1996) 1293:90-96.
Fernandes and Gregoriadis, BBA (1997) 1341:26-34.
Gregoriadis et al., FEBS Letters (1993) 315:271-276.
Jain et al., Drug Delivery Systems and Sciences (2004) 4(2):3-9.
Molineux, Curr. Pharm. Des., (2004) 10(11):1235-1244.
Park and Johnson, The Journal of Biological Chemistry (1949) 149-151.
Svennerholm, Biochemica et Biophysica Acta (1957) 24:604-611.
Wang, International Journal of Pharmaceutics (1999) 185:129-188.
International Search Report for PCT/GB2007/002816, mailed Dec. 12, 2007.

\* cited by examiner

*Primary Examiner* — Christine J Saoud
*Assistant Examiner* — Jegatheesan Seharaseyon
(74) *Attorney, Agent, or Firm* — One3 IP Management, P.C.; Annette S. Parent; Dean G. Stathakis

(57) ABSTRACT

The present invention relates to a compound which is a polysaccharide derivative of GCSF, or of a GCSF like protein, wherein the polysaccharide is anionic and comprises between 2 and 200 saccharide units. The present invention also relates to pharmaceutical compositions comprising the novel compounds, and methods for making the novel compounds.

9 Claims, 14 Drawing Sheets

42K CAO-GCSF Conj (PEG6K+Tween20)

42KCAO-GCSF Conj (Tween20)

42K CAO-GCSF Conj (PEG6K)

GCSF

MW Marker

SEQUENCE LISTING

<160> NUMBER OF SEQ ID NOS: 1

<210> SEQ ID NO 1
<211> LENGTH: 207
<212> TYPE: PRT
<213> ORGANISM: Homo sapiens

<400> SEQUENCE: 1

Met Ala Gly Pro Ala Thr Gln Ser Pro Met Lys Leu Met Ala Leu Gln
1               5                   10                  15

Leu Leu Leu Trp His Ser Ala Leu Trp Thr Val Gln Glu Ala Thr Pro
            20                  25                  30

Leu Gly Pro Ala Ser Ser Leu Pro Gln Ser Phe Leu Leu Lys Cys Leu
        35                  40                  45

Glu Gln Val Arg Lys Ile Gln Gly Asp Gly Ala Ala Leu Gln Glu Lys
    50                  55                  60

Leu Val Ser Glu Cys Ala Thr Tyr Lys Leu Cys His Pro Glu Glu Leu
65                  70                  75                  80

Val Leu Leu Gly His Ser Leu Gly Ile Pro Trp Ala Pro Leu Ser Ser
                85                  90                  95

Cys Pro Ser Gln Ala Leu Gln Leu Ala Gly Cys Leu Ser Gln Leu His
            100                 105                 110

Ser Gly Leu Phe Leu Tyr Gln Gly Leu Leu Gln Ala Leu Glu Gly Ile
        115                 120                 125

Ser Pro Glu Leu Gly Pro Thr Leu Asp Thr Leu Gln Leu Asp Val Ala
    130                 135                 140

Asp Phe Ala Thr Thr Ile Trp Gln Gln Met Glu Glu Leu Gly Met Ala
145                 150                 155                 160

Pro Ala Leu Gln Pro Thr Gln Gly Ala Met Pro Ala Phe Ala Ser Ala
                165                 170                 175

Phe Gln Arg Arg Ala Gly Gly Val Leu Val Ala Ser His Leu Gln Ser
            180                 185                 190

Phe Leu Glu Val Ser Tyr Arg Val Leu Arg His Leu Ala Gln Pro
        195                 200                 205

DERIVATISATION OF GRANULOCYTE COLONY-STIMULATING FACTOR

CROSS-REFERENCE TO RELATED APPLICATIONS

This application claims priority to U.S. Ser. No. 13/646,584 filed Oct. 5, 2012, which is a continuation of and claims priority to U.S. Ser. No. 12/375,006 filed Jan. 23, 2009, which is the national phase of PCT application PCT/GB2007/002816 having an international filing date of Jul. 25, 2007, which claims benefit of European patent application No. 06117830.7 filed Jul. 25, 2006. The contents of the above patent applications are incorporated by reference herein in their entirety.

REFERENCE TO A SEQUENCE LISTING

Sequence Listing file Name: 3IPXN1-0001USC2SeqList.txt

Sequence Listing file Size: 3 KB

The entire contents of the sequence listing are hereby expressly incorporated by reference.

The present invention relates to novel polysaccharide derivatives of GCSF and methods for producing such derivatives. The derivatives are useful for improving the stability, pharmacokinetics and pharmacodynamics of GCSF.

Granulocyte Colony-Stimulating Factor (GCSF, CSF3) is a glycoprotein. It may act as a hormone, growth factor or cytokine and is produced by a number of different tissues to stimulate the bone marrow to produce granulocytes and stem cells. GCSF also stimulates the survival, proliferation, differentiation, and function of neutrophil precursors and mature neutrophils.

GCSF is produced by endothelium, macrophages, and a number of other immune cells. The natural human glycoprotein exists in two forms, a 174- and 180-amino-acid-long protein of molecular weight 19,600 grams per mole. The more-abundant and more-active 174-amino acid form has been used in the development of pharmaceutical products by recombinant DNA (rDNA) technology. Mouse GCSF was first recognised and purified in Australia in 1983, and the human form was cloned by groups from Japan and the United States in 1986. The GCSF-receptor is present on precursor cells in the bone marrow, and, in response to stimulation by GCSF, initiates proliferation and differentiation into mature granulocytes.

GCSF stimulates the production of white blood cells. In oncology and hematology, a recombinant form of GCSF is used with certain cancer patients to accelerate recovery from neutropenia after chemotherapy, allowing higher-intensity treatment regimens. Chemotherapy can cause myelosuppression and unacceptably low levels of white blood cells, making patients prone to infections and sepsis. GCSF is also used to increase the number of hematopoietic stem cells in the blood before collection by leukapheresis for use in hematopoietic stem cell transplantation.

The recombinant human GCSF synthesised in an *E. coli* expression system is called filgrastim. The structure of filgrastim differs slightly from the structure of the natural glycoprotein. Most published studies have used filgrastim. Filgrastim (NEUPOGEN®) is a commercially-available form of rhGCSF (recombinant human GCSF).

Another form of recombinant human GCSF, lenograstim, is synthesised in Chinese Hamster Ovary cells. As this is a mammalian cell expression system, lenograstim is indistinguishable from the 174-amino acid natural human GCSF. No clinical or therapeutic consequences of the differences between filgrastim and lenograstim have yet been identified, and there have been no formal comparative studies.

Attempts have been made to derivatise GCSF to improve its pharmacokinetic properties. There is a product on the market, PEG-filgrastim (NEULASTA®), which is a polyethyleneglycol derivatised form of GCSF. This has been shown to have a longer half-life than filgrastim, reducing the necessity of daily injections. The design and development of PEG-filgrastim is described further in Curr. Pharm Des. 2004; 10(11): 1235-44.

US20070014759 describes conjugates between GCSF and PEG moieties which are linked via an intact glycosyl linking group. The conjugates are formed from both glycosylated and unglycosylated peptides by the action of a glycosyltransferase on mid-chain amino acids. U.S. Pat. No. 6,956,027 provides conditions for selectively modifying the N-terminus of GCSF with PEG.

Others have derivatised GCSF with molecules other than PEG. WO 2005/014050, for instance, describes GCSF covalently linked to hydroxyalkyl starch.

In view of the prior art, there is a need to provide improved derivatives of GCSF which can be used in human and animal therapy and have optimised stability, half-lives and low toxicity. We have found that attaching PSAs to GCSF imparts such properties and have thereby arrived at this invention. This is the first time that GCSF linked at the N-terminus to anionic polysaccharides has been described.

Polysialic acids (PSAs) are naturally occurring unbranched polymers of sialic acid produced by certain bacterial strains and in mammals in certain cells. They can be produced in various degrees of polymerisation from n=about 80 or more sialic acid residues down to n=2 by limited acid hydrolysis or by digestion with neuraminidases, or by fractionation of the natural, bacterially derived forms of the polymer.

In recent years, the biological properties of polysialic acids, particularly those of the alpha-2,8 linked homopolymeric polysialic acid, have been exploited to modify the pharmacokinetic properties of protein and low molecular weight drug molecules. Polysialic acid derivatisation gives rise to dramatic improvements in half-life for a number of circulating therapeutic proteins including catalase and asparaginase, and also allows such proteins to be used in the face of pre-existing antibodies raised as an undesirable (and sometimes inevitable) consequence of prior exposure to the therapeutic protein [Fernandes and Gregoriadis, 2006; Jain et. al., 2003, 2004]. The alpha-2,8 linked polysialic acid offers an attractive alternative to PEG, being an immunologically invisible biodegradable polymer which is naturally part of the human body, and which degrades, via tissue neuraminidases, to sialic acid, a non-toxic saccharide.

We have previously described methods for the attachment of polysaccharides (in particular PSA) to therapeutic agents such as proteins [U.S. Pat. No. 5,846,951; WO-A-0187922]. Some of these methods depend upon chemical derivatisation of the 'non-reducing' end of the polymer to create a protein-reactive aldehyde moiety which reacts at primary amine groups. A non-reducing sialic acid terminal unit, since it contains vicinal diols, can be readily (and selectively) oxidised with periodate to yield a mono-aldehyde form, which is much more reactive towards proteins, and which comprises a suitably reactive element for the attachment of proteins via reductive amination and other chemistries. The reaction is illustrated in FIGS. 1 and 2 wherein FIG. 1 shows the oxidation of colominic acid (alpha-2,8 linked polysialic acid from *E. coli*) with sodium periodate to form a protein-reactive aldehyde at the non-reducing end; and FIG. 2 shows the selective reduction of the Schiff's base with sodium cyanoborohydride to form a stable irreversible covalent bond with the protein amino group.

Unintentional by-products may be generated during the conventional conjugation reactions described above by reaction of the colominic acid with side chains of amino acids, for instance. These may be sufficient to be troublesome in the manufacture of chemically defined conjugates required by regulatory authorities for therapeutic use in man and animals.

It is not straightforward to purify the intended reaction product (for instance the monopolysialylated product) away from the various unintended products, since the physico-chemical characteristics of most of the reaction products are similar. This means that techniques such as ion-exchange chromatography and gel-permeation chromatography (which separate on the basis of charge and size respectively) produce poor purification profiles. This problem can be overcome by reducing the product complexity in the conjugation reaction. We have developed a new method for conjugation of polysaccharides to proteins whereby the high reactivity of the N-terminal of the protein can be utilized and which avoids the product complexity obtained using the established method (FIGS. 1 and 2) of reductive amination of proteins with periodate oxidised natural colominic acid.

In accordance with a first aspect of this invention we provide a compound which is an N-terminal polysaccharide derivative of GCSF, or of a GCSF like protein, wherein the polysaccharide is anionic and comprises between 2 and 200 saccharide units.

Hereinafter, when using the term GCSF, we also intend to cover GCSF-like proteins. By GCSF-like protein, we mean any biological compound possessing the activity of human granulocyte colony stimulating factor (a) whose amino acid sequence is at least fifty percent (50%) identical to SEQ I.D. No. 1, and (b) that has at least thirty-five percent (35%) preferably at least 50%, more preferably at least 60 or 70% human granulocyte colony stimulating factor activity as measured by a bioassay in comparison to the World Health Organization International Standard for human granulocyte colony stimulating factor (Human, rDNA-derived) as measured according to the bioassay described in Example 1.

GCSF-like proteins may also be referred to as "GCSF-homologues". Whether two sequences are homologues is routinely calculated using a percentage similarity or identity, terms that are well known in the art. Sequences should be compared to SEQ ID NO. 1, which is human GCSF with Swissprot accession number P09919. The active GCSF is residues 30-207 of this sequence. GCSF homologue sequences may either be compared to the whole of SEQ ID No. 1, or to residues 30-207 thereof. Preferably, the homologue is compared to the active GCSF.

In this invention homologues have 50% or greater similarity or identity at the amino acid level, more preferably 60%, 70%, 80% or greater, more preferably 90% or greater, such as 95% or 99% identity or similarity at the amino acid level. A number of programs are available to calculate similarity or identity; preferred programs are the BLASTn, BLASTP and BLASTx programs, run with default parameters, available at the NCBI website. For Example, 2 amino acid sequences may be compared using the BLASTn program with default parameters (score=100, word length=11, expectation value=11, low complexity filtering=on). The above levels of homology may be calculated using these default parameters.

The GCSF may be glycosylated or non-glycosylated.

In this invention, the term GCSF includes natural GCSF extracted from a human or mammalian body and synthetic versions thereof, such as recombinant human GCSF, for instance filgrastim and lenograstim as discussed above. Mutants of GCSF that have appropriate GCSF-like activity, such as cysteine mutants, are also included.

By "N-terminal derivative", we mean that the GCSF is derivatised by the anionic polysaccharide at its N-terminal amine group.

Preferably, the polysaccharide has at least 2, more preferably at least 5, most preferably at least 10, for instance at least 50 saccharide units.

The anionic polysaccharide is preferably selected from polysialic acid, heparin, hyaluronic acid and chondroitin sulphate. Preferably, the polysaccharide is polysialic acid and consists substantially only of sialic acid units. However, the polysaccharide may have units other than sialic acid in the molecule. For instance, sialic acid units may alternate with other saccharide units. Preferably, however, the polysaccharide consists substantially of units of sialic acid.

Preferably the polysaccharide has a terminal sialic acid group, and as detailed above, is more preferably a polysialic acid, that is a polysaccharide comprising at least 2 sialic acid units joined to one another through $\alpha$-2-8 or $\alpha$-2-9 linkages. A suitable polysialic acid has a weight average molecular weight in the range 2 to 200 kDa, preferably in the range 5 to 75 kDa. Most preferably, the polysialic acid is derived from a bacterial source, for instance polysaccharide B of *E. coli* K1, *N. meningitidis, Maraxella liquefaciens* or *Pasteurella aeruginosa* or K92 polysaccharide from *E. coli* K92 strain. It is most preferably colominic acid from *E. coli* K1.

The polysialic acid may be in the form of a salt or the free acid. It may be in a hydrolysed form, such that the molecular weight has been reduced following recovery from a bacterial source.

The polysaccharide, preferably polysialic acid, may be material having a wide spread of molecular weights such as having a polydispersity of more than 1.3, for instance as much as 2 or more. Preferably the polydispersity of molecular weight is less than 1.3 or 1.2, more preferably less than 1.1, for instance as low as 1.01.

Typically, the compound of this invention is a polysialic acid derivative of GCSF and comprises 80-180 sialic acid units. More typically, the compound comprises 100-150 sialic acid units. Preferably, the compound comprises 120-145, most preferably 130-140 sialic acid units.

The compound according to the first aspect of this invention may be a covalently-linked conjugate between the N-terminus of GCSF or a GCSF-like protein and an anionic polysaccharide. Other means of association between the polysaccharide and the GCSF include electrostatic attraction. However, covalent bonding is preferred. The covalent linkage may be an amide linkage between a carboxyl group and an amine group. Another linkage by which the GCSF could be covalently bonded to the polysaccharide is via a Schiff base. Suitable groups for conjugating to amines are described further in WO 2006/016168.

The polysaccharide may be linked to the GCSF via either its reducing or non-reducing terminal unit. One polysaccharide chain may be linked at both terminal units to GCSF proteins. This means that one polysaccharide chain may be linked to two GCSF proteins, i.e. be derivatised at both its reducing and non-reducing end.

In the invention the polysaccharide may be a naturally occurring polysaccharide, or a derivative of a naturally occurring polysaccharide, for instance, a polysaccharide which has been derivatised by a reaction of one or more active groups on the saccharide residues, or which has been covalently linked to a derivatising group at the end of the polysaccharide chain.

Methods for attaching polysaccharides to proteins are well known in the art and are described in more detail in WO 92/22331 and WO-A-0187922. The preferred methods in this invention are described in more detail below. Methods are also described in FIGS. 1 and 2 of this application.

The polysaccharide may be linked to the GCSF or GCSF-like protein directly, i.e. as shown in FIGS. 1 and 2, or via a linker. Suitable linkers are derived from N-maleimide, vinylsulphone, N-iodoacetamide, orthopyridyl or N-hydroxysuccinimide-containing reagents. The linker may also be biostable or biodegradable and comprise, for instance, a polypeptide or a synthetic oligomer. The linker may be derived from a bifunctional moiety, as further described in WO 2005/016973. A suitable bifunctional reagent is, for instance, Bis-NHS. The reagent may have general formula Z—R$^1$—Z wherein each Z is a functional group and may be the same or different and R$^1$ is a bifunctional organic radical. Preferably, R$^1$ is selected from the group consisting of alkanediyl, arylene, alkarylene, heteroarylene and alkylheteroarylene, any of which may substituted and/or interrupted by carbonyl, ester, sulfide, ether, amide and/or amine linkages. Particularly preferred is $C_3$-$C_6$ alkanediyl. Most preferably, R$^1$ corresponds to the appropriate portion of the suitable bifunctional reagent We provide in accordance with a second aspect of this invention a compound of general formula (I)

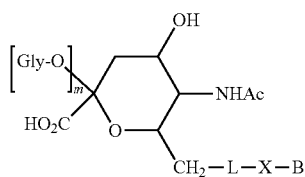

(I)

wherein m is at least one;
XB is derived from B—XH which is GCSF or a GCSF-like protein wherein XH is $NH_2$ or SH;
L is a bond, a linking group, or comprises a polypeptide or a synthetic oligomer;
GlyO is an anionic saccharide unit;
wherein the linking group, if present, is of general formula
—Y—C(O)—R$^1$—C(O)—;
wherein Y is N R$^2$ or N R$^2$—N R$^2$ and R$^1$ is a difunctional organic radical as defined above; and R$^2$ is H or $C_{1-6}$ alkyl.

In this aspect of the invention the GCSF is linked to the non-reducing end of the polysaccharide. The terminal polysaccharide unit is a sialic acid unit. The other saccharide units in the polysaccharide are represented by GlyO and may be the same or different. Suitable saccharide units include heparin, hyaluronic acid or chondroitin sulphate.

When the GCSF is attached directly to the polysaccharide, the group L is a bond. However, the group L may alternatively be derived from an N-maleimide, vinylsulphone, N-iodoacetamide, orthopyridyl or N-hydroxysuccinimide containing reagent. The reagent may have general formula Z—R$^1$—Z as defined above. In this embodiment, L is typically a group

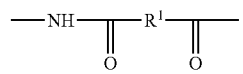

Preferably, XH is $NH_2$ and is the N-terminal amine of the GCSF or GCSF-like protein. Alternatively, $NH_2$ may be the primary amine of a lysine amino acid side chain. In a different embodiment, XH is a thiol group, SH, from the side chin of a cysteine amino acid.

Another aspect of the invention is a pharmaceutical composition comprising a novel compound as defined above and one or more pharmaceutically acceptable excipients.

The pharmaceutical composition may be in the form of an aqueous suspension. Aqueous suspensions contain the novel compounds in admixture with excipients suitable for the manufacture of aqueous suspensions. The pharmaceutical compositions may be in the form of a sterile injectable aqueous or homogeneous suspension. This suspension may be formulated according to the known art using suitable dispersing or wetting agents and suspending agents.

Pharmaceutical compositions may be administered orally, intravenously, intraperitoneally, intramuscularly, subcutaneously, intranasally, intradermally, topically or intratracheally for human or veterinary use.

The compositions may further comprise a formulation additive. By formulation additive we mean an excipient which is capable of stabilising the GCSF either internally or externally, as described in Wang et al (1999). The excipient may be a stabiliser, a solubilser or a metal ion. Suitable examples of formulation additives include one or more buffers, stabilisers, surfactants, salts, polymers, metal ions, sugars, polyols or amino acids. These may be used alone or in combination.

Stabilisers typically act by destabilisation of the denatured state of a protein leading to increased Gibbs free energy change for unfolding of the protein. The stabiliser is preferably a sugar or a polyol, for example sucrose, sorbitol, trehalose, glycerol, mannitol, lactose and ethylene glycol. A stabilising buffer is sodium phosphate.

The solubiliser is preferably a surfactant, preferably a non-ionic surfactant. Suitable examples include Tween 80, Tween 20, Tween 40, Pluronic F68, Brij 35 and Triton X100.

The metal ion is preferably divalent. Suitable metal ions include $Zn^{2+}$, $Ni^{2+}$, $Co^{2+}$, $Sr^{2+}$, $Cu^{2+}$, $Ca^{2+}$, $Mg^{2+}$ and $Fe^{2+}$.

The formulation additive may also be a polymer selected from PSA, PEG or hydroxy-beta-cyclodextrin.

Suitable amino acids and amino acid derivatives for use as the formulation additive include histidine, glycine, other similar amino acids and sodium aspartate.

Another aspect of this invention is a composition comprising a population of anionic polysaccharide derivatives of GCSF or a GCSF-like protein, wherein the derivatives comprise between 2 and 200 saccharide units and wherein the population consists substantially only of N-terminal derivatives of the protein.

By "population" we mean that there is more than one polysaccharide derivative in the composition. The derivatives may comprise the same or different numbers of saccharide units. Preferably, the polydispersity of the polysaccharide in the composition is less than 1.3, more preferably less than 1.1. Preferred polysaccharides are as detailed above for the other aspects of this invention.

In the population, substantially all of the GCSF is derivatised at the N-terminal amine only. By this, we mean that 85%, preferably at least 90%, most preferably at least 95% of the protein in the population is derivatised with PSA at the N-terminal amine only.

The degree of derivatisation at the N-terminus can be measured using techniques well known in the art, such as peptide mapping and Edman Degradation.

A further aspect of the invention is a compound as described above for use in therapy.

In accordance with a final aspect of the invention, we provide a method for producing a polysaccharide derivative of GCSF or of a GCSF-like protein wherein an anionic polysaccharide comprising 2-200 saccharide units is chemically reacted with the GCSF or GCSF-like protein.

It will be noted in this aspect of the invention, the polysaccharide may react at any group on the GCSF or GCSF-like protein. For instance, the polysaccharide may react with an amine, amide, aryl, aldehyde, ketone, guanidino, midazole, hydroxyl, carboxyl or sulfhydryl group. Preferably, the group is an amine group, more preferably a terminal amine group. The amine may alternatively be the amine side chain of an amino acid, such as a lysine amino acid. The polysaccharide may also react at any carbohydrate residues on the GCSF, such as on pendant glycon groups.

Polysaccharides may be linked to amino acid side chains by methods know in the art. For instance, a polysaccharide may be coupled to the C-terminus, —COOH or carboxyl side chains of Asp or Glu by in vitro coupling. Thiol groups of cysteine amino acids may also be linked to polysaccharides by in vitro coupling. These methods are described further in WO03/055526, in particular the table on pages 6 and 7. In this reference, in vitro coupling is also used to link an oligosaccharide moiety to the amide group on the side chain of Gln. In vitro coupling methods for linking of oligosaccharide moieties to guanidino and imidazole groups of Arg and H is residues respectively are also described. Each of these methods may be used to derivatise the GCSF of the present invention.

The polysaccharide may also react with a modified form of GCSF. For instance, one or more groups on the GCSF may have undergone a chemical transformation, for instance, by reduction or oxidation. A reactive carbonyl may be generated in the place of the terminal amino group of GCSF using oxidation conditions, for instance.

Suitable polysaccharides for use in the method of this invention are as described previously for the novel compounds.

The compounds of the invention may be manufactured by any of the suitable methods described in the prior art. For example, a typical method is described to our previous patent application WO 92/22331.

Typically, the anionic polysaccharide has been activated before derivatisation to GCSF. It may, for instance, have a reactive aldehyde group and the derivatisation reaction may be carried out under reducing conditions. The reactive aldehyde group may be produced by controlled oxidation of a hydroxyl group of the polysaccharide. Most preferably this reactive aldehyde is generated in a preliminary step, in which the polysaccharide is reacted under controlled oxidation conditions, for instance using sodium periodate, in aqueous solution. Preferably the oxidation is a chemical oxidation, although enzymes which are capable of carrying out this step may also be used. The reactive aldehyde group may be at the non-reducing end or reducing end of the polysaccharide. The GCSF, typically the N-terminus, may then react with the reactive aldehyde group to produce an adduct which, when reduced, produces the N-terminal derivative of GCSF.

The activation of the polysaccharide should preferably be carried out under conditions such that there is substantially no mid-chain cleavage of the backbone of the polysaccharide, that is substantially no molecular weight reduction. The oxidant is suitably perrhuthenate, or, preferably, periodate. Oxidation may be carried out with periodate at a concentration in the range 1 mM to 1M, at a pH in the range 3 to 10, a temperature in the range 0 to 60.degree. C. for a time in the range 1 min to 48 hours.

Suitable reduction conditions for the derivatisation reaction may utilise hydrogen with catalysts or, preferably hydrides, such as borohydrides. These may be immobilised such as AMBERLITE™ (an anion exchange resin)-supported borohydride. Preferably alkali metal hydrides such as sodium borohydride is used as the reducing agent, at a concentration in the range 1 µM to 0.1M, a pH in the range 5.0 to 10, a temperature in the range 0 to 60° C. and a period in the range 1 min to 48 hours. The reaction conditions are selected such that pendant carboxyl groups on the starting material are not reduced. Other suitable reducing agents are cyanoborohydride under acidic conditions, e.g. polymer supported cyanoborohydride or alkali metal cyanoborohydride, L-ascorbic acid, sodium metabisulphite, L-selectride, triacetoxyborohydride etc.

Other activated derivatives of polysaccharides may have utility in the present invention, including those with pendant functional groups such as NHS, as described in our earlier patent application WO 06/00540.

In one embodiment, the reactive aldehyde is at the reducing end of the polysaccharide and the non-reducing end has been passivated such that it does not react with pendant groups on the GCSF.

The reactivity of the reducing end of colominic acid, though weak towards protein targets, is sufficient to be troublesome in the manufacture of chemically defined conjugates.

Chemistry suitable for preparing a polysaccharide with a reactive aldehyde at the reducing terminal of a polysaccharide is described in our earlier application WO 05/016974. The process involves a preliminary selective oxidation step followed by reduction and then further oxidation to produce a compound with an aldehyde at the reducing terminal and a passivated non-reducing end.

WO 2005/016973 describes polysialic acid derivatives that are useful for conjugation to proteins, particularly those which have free sulfhydryl drugs. The polysialic acid compound is reacted with a heterobifunctional reagent to introduce a pendant functional group for site-specific conjugation to sulfhydryl groups. The anionic polysaccharides used in the present invention may also be derivatised with a heterobifunctional reagent in this manner.

The polysaccharide may be derivatised before it reacts with GCSF. For instance, the polysaccharide may react with a bifunctional reagent.

The polysaccharide may be subjected to a preliminary reaction step, in which a group selected from a primary amine group, a secondary amine group and a hydrazine is formed on the terminal saccharide, which is preferably sialic acid, followed by a reaction step in which this is reacted with a bifunctional reagent to form a reaction-intermediate, as further described in WO 2006/016168. The intermediate may then react with the GCSF or GCSF-like protein. The bifunctional reagent may have general formula Z—$R^1$—Z, as defined previously.

We have found that certain reaction conditions promote selective derivatisation at the N-terminal of the GCSF. To promote selective reaction at the N-terminal, the derivatisation reaction should be carried out in a first aqueous solution of acidic pH, and the resultant polysaccharide derivative should then be purified in a second aqueous solution of higher pH than the first aqueous solution. Typically the pH of the first aqueous solution is less than 7, and is preferably in the range 4.0-6.0. The pH of the second aqueous solution is in the range of 6.5-9.5, preferably 6.5-8.5. The low pH of the derivatisation reaction promotes selective derivatisation at the N-terminus of the protein rather than at any mid-chain sites.

Furthermore, we have found that the use of certain formulation additives promotes the formation of a selective, stable, polysaccharide GCSF-derivative. The formulation additive may be selected from one or more buffers, stabilisers, surfactants, salts, polymers, metal ions, sugars, polyols or amino acids. These may be added to the reaction medium, or alternatively may be added to the final product composition, as a stabiliser.

In one embodiment of this invention, the formulation additive is sorbitol, mannitol, trehalose or sucrose. In a different embodiment, the formulation additive is a non-ionic surfactant. The formulation additive may alternatively be a polymer selected from PSA, PEG or hydroxy-beta-cyclodextrin e.g. Tween 20, Tween 80, PEG. In a different embodiment the formulation additive is a divalent metal ion. Preferred divalent metal ions include $Zn^{2+}$, $Ni^{2+}$, $Co^{2+}$, $Sr^{2+}$ or $Fe^{2+}$.

The formulation additive may be a buffer. Preferably when the formulation additive is a buffer, it is sodium phosphate or sodium acetate.

The purification of the polysaccharide derivative in the method of the present invention may be carried out using a variety of methods known in the art. Examples of suitable purification methods include HIC (hydrophobic interaction chromatography), SEC (size exclusion chromatography), HPLC (high performance liquid chromatography), AEX (anion exchange chromatography) and MAC (metal affinity chromatography).

A population of polysialic acids having a wide molecular weight distribution may be fractionated into fractions with lower polydispersities, i.e. into fractions with differing average molecular weights. Fractionation is preferably performed by anion exchange chromatography, using for elution a suitable basic buffer, as described in our earlier patent applications WO 2005/016794 and WO 2005/03149. The fractionation method is suitable for a polysaccharide starting material as well as to the derivatives. The technique may thus be applied before or after the essential process steps of this invention. Preferably, the polydispersity of the resultant polysaccharide derivative of GCSF is less than 1.1.

The derivatisation of GCSF in accordance with this invention, results in increased half-life, improved stability, reduced immunogenicity, and/or control of solubility and hence bioavailability and the pharmacokinetic properties of GCSF. The new method is of particular value for creation of a monopolysialylated-GCSF conjugates.

The invention is illustrated by Examples 1-10 and by reference to the following drawings:—

EXAMPLES

Materials

Figure 1:
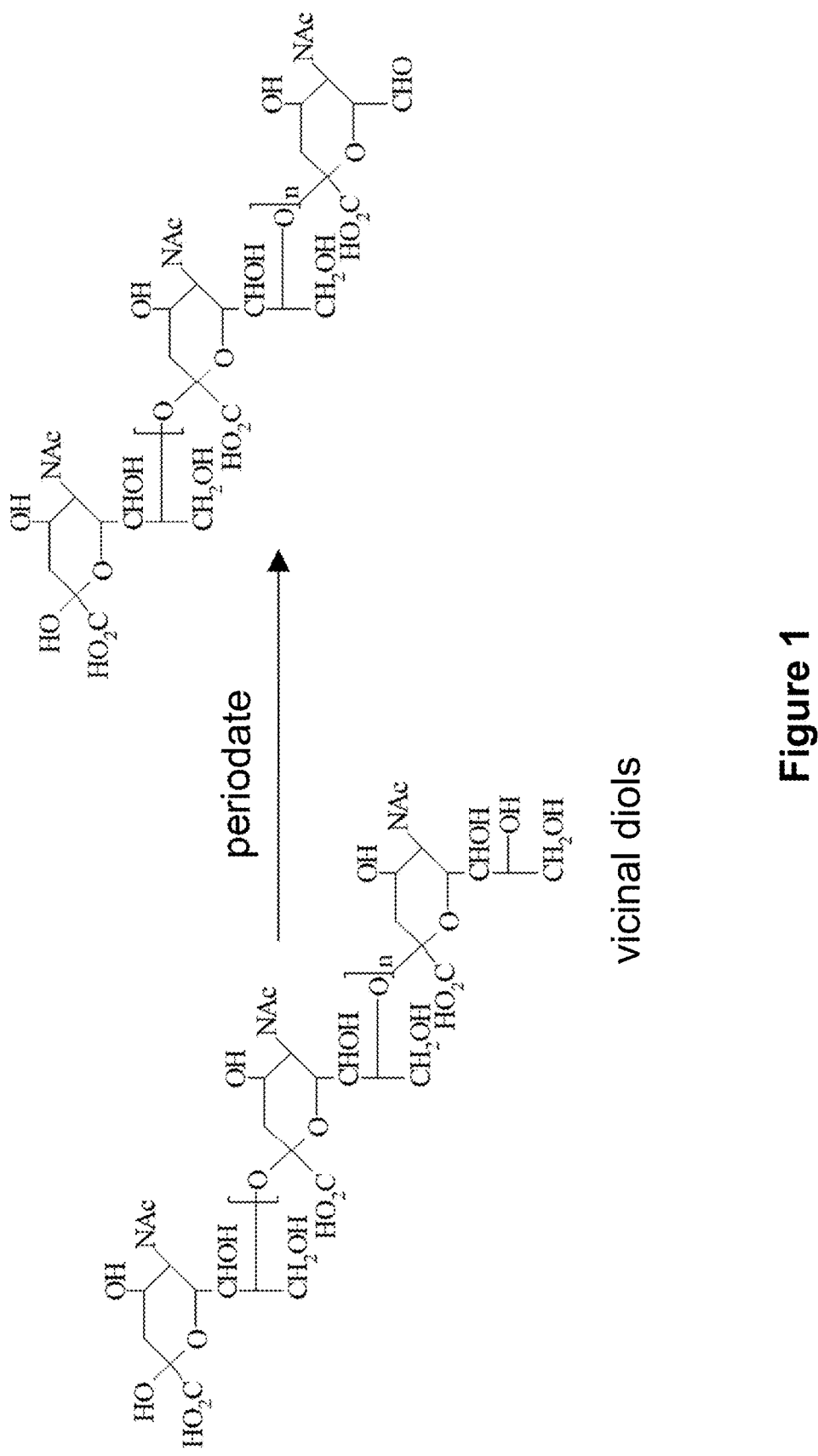
FIG. 1 is a reaction scheme showing the prior art activation of the non-reducing sialic acid terminal unit.
Figure 2:
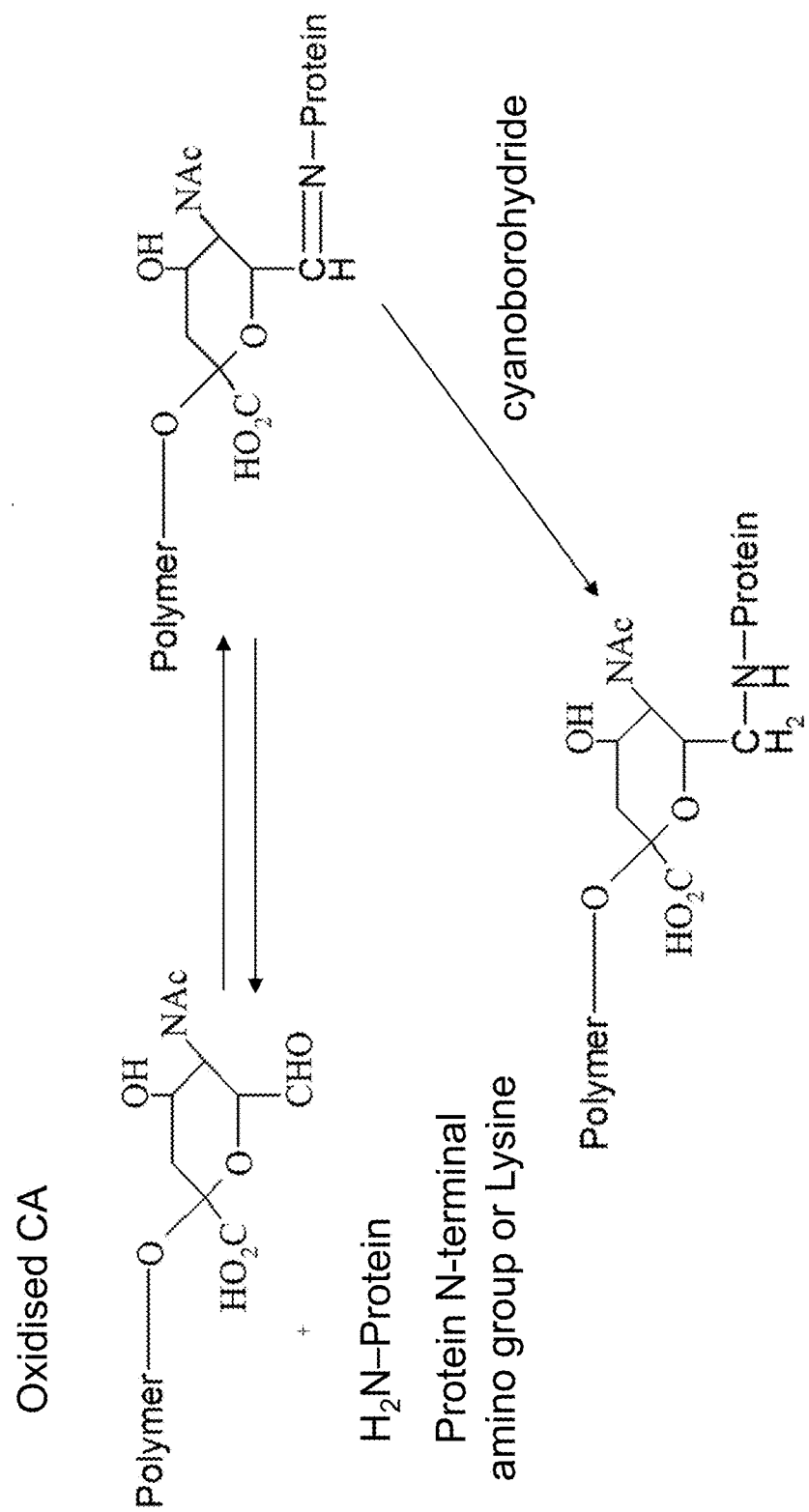
FIG. 2 is a reaction scheme showing the N-terminal or random derivatization of proteins.

Ammonium carbonate, ethylene glycol, polyethylene glycol (8 KDa), sodium cyanoborohydride (>98% pure), sodium meta-periodate and molecular weight markers, ammonium sulphate, sodium chloride, sodium phosphate, sorbitol, Tween 20 and Tris were obtained from Sigma Chemical Laboratory, UK. Sodium acetate and sodium phosphate were from BDH, UK. The colominic acid used, linear alpha-(2,8)-linked *E. coli* K1 polysialic acids (22.7 kDa average, high polydispersity 1.34, 39 kDa p.d. 1.4; 11 kDa, p.d. 1.27) was from Camida, Ireland. Other materials included 2,4 dinitrophenyl hydrazine (Aldrich Chemical Company, UK), dialysis tubing (3.5 KDa and 10 KDa cut off limits; Medicell International Limited, UK), Sepharose SP HiTrap, PD-10 columns, Q FF [column 1 ml or 5 ml]; Hitrap Butyl HP column [1 or 5 ml]; (Pharmacia, UK), Tris-glycine polyacrylamide gels (4-20% and 16%), Tris-glycine sodium dodecylsulphate running buffer and loading buffer (Novex, UK). Deionised water was obtained from an Elgastat Option 4 water purification unit (Elga Limited, UK). All reagents used were of analytical grade. A plate reader (Dynex Technologies, UK) was used for spectrophotometric determinations in protein or CA assays. Mice were purchased from Harlan, UK and acclimatized for at least one week prior to their use. GCSF was obtained from SIIL, India.

Example 1

GCSF Bioassay

G-CSF biological activity determination is based on stimulation of M-NFS-60 cells proliferation by this cytokine. Cells are incubated with serial dilutions of both reference and G-CSF preparations for 48 hours. Cells proliferative response is estimated after 4 hours incubation with viable cells dyeing system—PMS (electron coupling reagent) mixture. MTS is bioreduced by cells into formazan product that is soluble in tissue culture medium. The absorbance of formazan at 492 nm can be measured directly from 96 well assay plates without additional processing. The quantity of formazan product, as measured by the amount of 492 nm absorbance, is directly proportional to the number of living cells.

The World Health Organisation International Standard for GCSF (human rDNA-derived) 88/502, 10,000 IU/ampoule, content 100 ng G-CSF, NIBSC, UK should be used as the reference.

Example 2

Protein and Colominic Acid Determination

Quantitative estimation of polysialic acids (as sialic acid) with the resorcinol reagent was carried out by the resorcinol method [Svennerholm, 1957] as described elsewhere [Gregoriadis et al., 1993; Fernandes and Gregoriadis, 1996, 1997]. Protein was measured by the BCA colorimetric method or UV absorbance at 280 nm.

2.1 Activation of Colominic Acid

Freshly prepared 0.02 M sodium metaperiodate (NaIO$_4$) solution (8 fold molar excess) was mixed with CA at 20° C. and the reaction mixture was stirred magnetically for 15 min in the dark. A two-fold volume of ethylene glycol was then added to the reaction mixture to expend excess NaIO$_4$ and the mixture left to stir at 20° C. for a further 30 min. The oxidised colominic acid was dialysed (3.5 KDa molecular weight cut off dialysis tubing) extensively (24 h) against a 0.01% ammonium carbonate buffer (pH 7.4) at 4° C. Ultrafiltration (over molecular weight cut off 3.5 kDa) was used to concentrate the CAO solution from the dialysis tubing. Following concentration to required volume, the filterate was lyophilized and stored at 40° C. until further use. Alternatively, CA was recovered from the reaction mixture by precipitation (twice) with ethanol.

2.2 Determination of the Oxidation State of CA and Derivatives

Qualitative estimation of the degree of colominic acid oxidation was carried out with 2,4 dinitrophenylhydrazine (2,4-DNPH), which yields sparingly soluble 2,4 dinitrophenyl-hydrazones on interaction with carbonyl compounds. Non-oxidised (CA)/oxidised (CAO) were added to the 2,4-DNPH reagent (1.0 ml), the solutions were shaken and then allowed to stand at 37° C. until a crystalline precipitate was observed [Shriner et. al., 1980]. The degree (quantitative) of CA oxidation was measured with a method [Park and Johnson, 1949] based on the reduction of ferricyanide ions in alkaline solution to ferric ferrocyanide (Persian blue), which is then measured at 630 nm. In this instance, glucose was used as a standard.

2.3 Gel Permeation Chromatography

Colominic acid samples (CA and CAO) were dissolved in NaNO$_3$ (0.2M), CH$_3$CN (10%; 5 mg/ml) and were chromatographed on over 2×GMPW$_x$L columns with detection by refractive index (GPC system: VE1121 GPC solvent pump, VE3580 RI detector and collation with Trisec 3 software (Viscotek Europe Ltd). Samples (5 mg/ml) were filtered over 0.45 μm nylon membrane and run at 0.7 cm/min with 0.2M NaNO$_3$ and CH$_3$CN (10%) as the mobile phase.

Figure 3A:
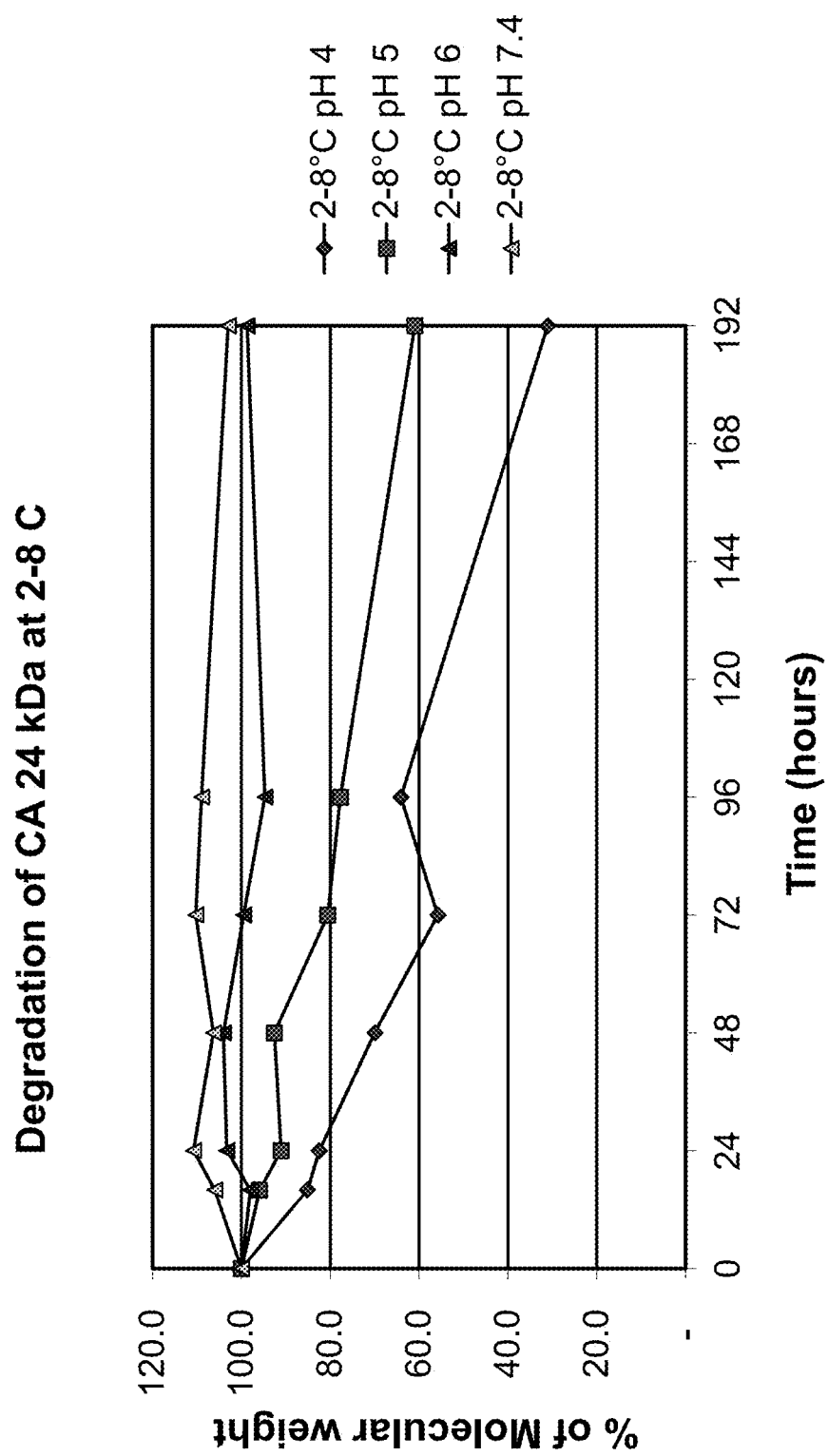
FIG. 3a shows the degradation of 24 kDa colominic acid (CA) at different pHs using Triple Detection GPC (Viscotek: RI+RALS+Viscosiometer)
Figure 3B:
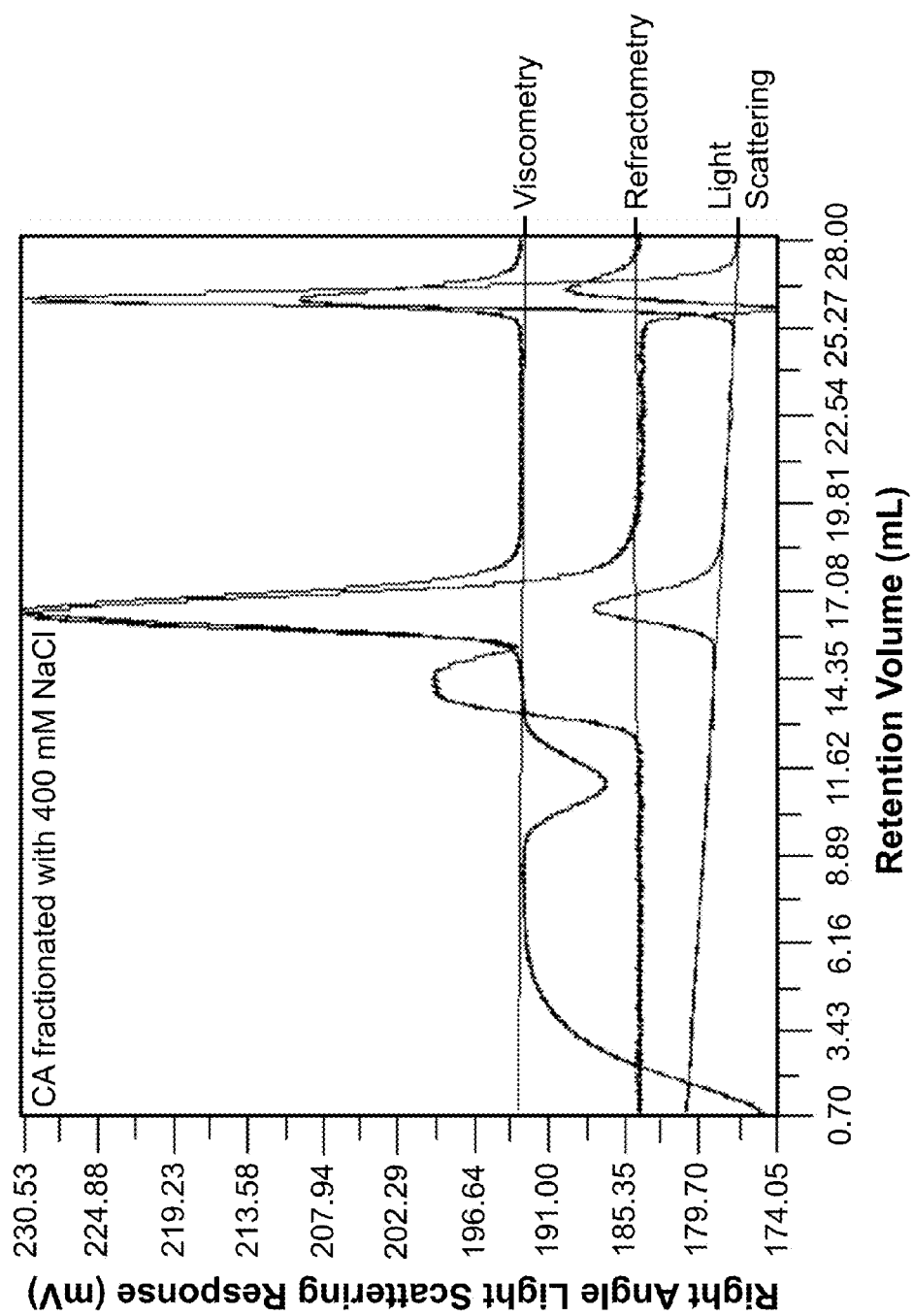
FIG. 3b shows the results of GPC chromatography of CA fractionated with 400 mM NaCl.

The results are shown in FIG. 3*b* and tables 4 and 5 (see page 25).

2.4 Colominic Acid Stability

The rules for chemistry of the PEGylation cannot be applied to polysialylation as such because of the difference in the physiochemical properties of these molecules. PSA is an acid labile polymer and is stable for weeks around neutral pH (FIG. 3*a*). The results in FIG. 3*a* show that at pH 6.0 and 7.4 CA is stable for 8 days, at pH 5.0 there is slow degradation (after 48 hours 92% of initial MW), and at pH 4.0 there is slow degradation (after 48 hours 70% of initial MW). Polysialic acid is highly hydrophilic whereas PEG is an amphiphilic molecule in nature. When the polysialylation is carried out using conditions used for PEGylation, aggregation and precipitation of the proteins is seen in many cases.

Example 3

Preparation of N-Terminal Protein-CA Conjugates with Formulation Additives 3.1 Preparation of GCSF-CA Conjugates (N-Terminal Method)

GCSF (18.8 kDa) was supplied as a solution (1.05 mg/ml in 10 mM sodium acetate buffer, pH 4.0 containing 5% sorbitol, 0.025 mg/ml polysorbate 80) and stored at 2-8° C. The required amount of GCSF was taken into an eppendorf and placed on ice. The amount of CA to be added for conjugation was calculated based on formula:

$$\text{Weight of } CA = \frac{\text{Amount of protein (g)}}{\text{(MW of protein)}} \times (\text{MW of } CA) \times (\text{Molar excess of } CA)$$

Required amount of CA was weighed out. CA was solubilised in 10 mM NaOAc, 5% sorbitol, pH 5.5 (20% volume of the final reaction volume was used here), gently vortexed the mixture until all the CA has dissolved and then either filtered into a new eppendorf or centrifuged at 4000 rpm for 5 min and the supernatant was transferred to a new eppendorf to remove any aggregated/precipitated material. Required volume of 10 mg/ml Tween 20 stock solution was added, in order to have a final concentration of 0.5 mg/ml of the Tween 20 in the final reaction mixture. Required amount of GCSF protein solution was added to the CA solution to give a 10 molar excess (small scale) and 9 (large scale) of CA and gently mixed by keeping the reaction mixture on a gentle shaker at 4±1° C. 100 mg/ml NaCNBH$_3$ solution was added in order to have 50 mM or 3.17 mg/ml in the final reaction mixture, gently mixed and pH of the final reaction mixture was checked, if necessary adjusted the pH to 5.5 with 1 M NaOH/HCl at 4±1° C. Finally adjusted the volume of the reaction using 10 mM NaOAc, 5% sorbitol, pH 5.5 to give a protein concentration of 0.67 mg/ml in the reaction mixture. Tube was sealed and stirred at desired temperature (4±1° C.) for 24 hours. The reaction was stopped by an appropriate method and samples were taken out for in vitro activity assay on MNFS 60 cell, SDS-PAGE (using 4-20% Tris glycine gel), SE-HPLC (superose 6 column) and checked the pH of reaction mixture. To eliminate any precipitate the reaction mixture was centrifuged at 13000 rpm for 5 min before SE-HPLC analysis and purification, preferred buffer for SE-HPLC was 0.1 M Na phosphate (pH 6.9).

Optimisation

Reductive amination was performed with a range of molecular weights of CA (29-52 kda) on GCSF for N-terminal and random derivatisation. Range of process variables were studied for conjugation reactions: CAO 10-20 (small scale) and 8-15 (large scale) molar excess; reagent=50-100 mM NaCNBH$_3$; reaction buffer=10 mM NaOAc; pH 5.0-7.4, formulation additives=Tween 20 6 KDa/Peg 8 KDa (10M excess)/Tween 20+PEG 6 KDa; temperature=4±1° C., time=16-24 hours etc.

Optimised reaction conditions were found to be as following: CAO=10 (small scale) and 9 (large scale) molar excess, reagent=50 mM NaCNBH$_3$, Reaction buffer=10 mM NaOAc pH 5.5, additives=0.5 mg/ml, tween 20, temperature=4±1° C., time=22 hours.

3.2. Purification and Characterization of GCSF-CA Conjugates (N-Terminal Method)

The remaining reaction mixture sample was diluted with AEX buffer A (20 mM sodium acetate, 50 mM sodium chloride pH 5.0) (1.5 ml reaction mixture+9 ml of buffer A), the pH was checked and adjusted if required to pH 5.0, and loaded on the AEX column previously equilibrated with AEX buffer A. The loading fractions were collected and labelled. The column was washed with AEX buffer A (at least 5 column volume), fractions were collected (each fraction 1.5 column volume) and labelled. The product was eluted with AEX buffer B (50 mM sodium phosphate, 0.65 M sodium chloride, pH 7.0), fractions were collected (each fraction 1 column volume; 6 column) and labelled. If two consecutive fractions had no protein content (UV280 nm), the next step was carried out. The samples were kept on ice during purification. The protein concentration was analysed by UV (280 nm) (Abs of 1 mg/ml of GCSF was about 0.872). The samples were taken for SDS-PAGE and SE-HPLC. To remove free CA from the mixture, HIC was used. The samples were concentrated, if required.

The AEX fractions containing conjugate were pooled and (NH$_4$)$_2$SO$_4$ added to give a concentration of 2.75 M in the loading solution. This solution was then loaded on to the HIC column previously equilibrated with HIC buffer A (10 mM sodium phosphate, 2.75 M ammonium sulphate, pH 6.5). The loading fractions were collected (each fraction 1.5 column volume) and labelled. The column was washed with HIC buffer A (at least 5 column volumes; rate=0.5 ml/min; (1.5 column volume) fractions collected and labelled. The product was eluted with HIC buffer B (20 mM sodium phosphate pH 7.4) (rate=5 ml/min); fractions were collected (1 column volume fraction; 6 column volume) and labelled. Samples were kept on ice during purification. Protein concentration was analyzed by UV (280 nm). The HIC fractions containing the purified conjugate were combined and composition of the conjugate in solution was adjusted with 50% sorbitol solution and 10 mg/ml Tween 20 solution to give a final composition of 5% sorbitol and 0.025 mg/ml Tween 20. The solution was then concentrated at 4±1° C. and the protein concentration analysed by UV (280 nm). Further purification was done by SE-HPLC (e.g. to separate conjugates from free protein/aggregates etc.). Conjugate were sterile filtered and samples taken for activity assay and for characterisation by SDS-PAGE and SE-HPLC. If required an aliquot was removed for a protein assay and CA assay. The remainder was stored at 4±1° C. until further use and studied for physical stability by SE-HPLC.

The effects of various processes affecting the stability of GCSF in solution and the degree of derivatization were studied.

3.3.1. Preparation of GCSF-CA Conjugates (Random)

GCSF (18.8 kDa) was supplied as a solution (1.05 mg/ml in 10 mM sodium acetate buffer, pH 4.0 containing 5% sorbitol, 0.025 mg/ml polysorbate 80) and stored at 2-8.degree. C. The required amount of GCSF was taken into an eppendorf and placed on ice. The amount of CA (e.g. oxidised or non-oxidised CA) to be added for conjugation was calculated based on formula:

$$\text{Weight of } CA = \frac{\text{Amount of protein (g)}}{\text{(MW of protein)}} \times (\text{MW of } CA) \times (\text{Molar excess of } CA)$$

The required amount of CA was weighed out. The CA was solubilised in 50 mM sodium phosphate, 5% sorbitol, pH 7.4 (20% volume of the final reaction volume was used here). The mixture was gently vortexed until all the CA has dissolved and then either filtered into a new eppendorf or centrifuged at 4000 rpm for 5 min and the supernatant transferred to a new eppendorf to remove any aggregated/precipitated material. The required volume of 10 mg/ml Tween 20 stock solution was added, in order to have a final concentration of 0.5 mg/ml of the Tween 20 in the final reaction mixture. The required amount of GCSF protein solution was added to the CA solution to give a 11 molar excess (for 40 kDa) of CA and gently mixed by keeping the reaction mixture on a gentle shaker at 4±1° C. 100 mg/ml NaCNBH$_3$ solution was added in order to have 50 mM or 3.17 mg/ml in the final reaction mixture, gently mixed and pH of the final reaction mixture was checked, if necessary adjusted the pH to 7.4 with 1 M NaOH/HCl at 4±1° C. Finally adjusted the volume of the reaction using 10 mM NaOAc, 5% sorbitol, pH 7.4 to give a protein concentration of 0.67 mg/ml in the reaction mixture. Tube was sealed and stirred at desired temperature (4±1° C.) for 22 hours. The reaction was stopped by an appropriate method and samples were taken out for in vitro activity assay on MNFS 60 cells, SDS-PAGE (using 4-20% Tris glycine gel), SE-HPLC and the pH of reaction mixture was checked. To eliminate any precipitate the reaction mixture was centrifuged at 13000 rpm for 5 min before SE-HPLC analysis and purification, preferred buffer for SE-HPLC was 0.1 M Na phosphate (pH 6.9).

3.3.2. Purification and Characterization of GCSF-CA Conjugates (Random)

Monosialylated GCSF conjugates were purified from the other GCSF conjugates by HIC and IEC. The remaining reaction mixture sample was diluted with AEX buffer A (20 mM sodium acetate, 50 mM sodium chloride pH 5.0) (1.5 ml reaction mixture+9 ml of buffer A), the pH was checked and adjusted if required to pH 5.0 and loaded on the AEX column previously equilibrated with AEX buffer A. The loading fractions were collected and labelled. The column was washed with AEX buffer A (at least 5 column volume), fractions collected (each fraction 1.5 column volume) and labelled. The product was eluted with AEX buffer B (50 mM sodium phosphate, 0.65 M sodium chloride, pH 7.0), fractions collected (each fraction 1 column volume; 6 column) and labelled. If two consecutive fractions had no protein content (UV280 nm), the next step was followed. Samples were kept on ice during purification. The protein concentration was analysed by UV (280 nm) (Abs of 1 mg/ml of GCSF was about 0.872). The samples were taken for SDS-PAGE and SE-HPLC. To remove free CA from the mixture, HIC was used. Samples were concentrated, if required.

The AEX fractions containing conjugate were pooled and (NH$_4$)$_2$SO$_4$ was added to give a concentration of 2.75 M in the loading solution. This solution was then loaded on to the HIC column previously equilibrated with HIC buffer A (10 mM Sodium Phosphate, 2.75 M ammonium sulphate, pH 6.5). The loading fractions were collected (each fraction 1.5 column volume) and labelled. The column was washed with HIC buffer A (at least 5 column volumes; rate=0.5 ml/min. (1.5 column volume) fractions were collected and labelled. The product was eluted with HIC buffer B (20 mM sodium phosphate pH 7.4) (rate=5 ml/min); fractions collected (1 column volume fraction; 6 column volume) and labelled. Samples were kept on ice during purification. The protein concentration was analyzed by UV (280 nm). The HIC fractions containing the purified conjugate were combined and the composition of the conjugate in solution was adjusted with 50% sorbitol solution and 10 mg/ml Tween 20 solution to give a final composition of 5% sorbitol and 0.025 mg/ml Tween 20. The solution was then concentrated at 4±1° C. and the protein concentration was analysed by UV (280 nm). Further purification was done by SE-HPLC (e.g. to separate conjugates from free protein/aggregates etc.). The conjugates were sterile filtered and samples taken for activity assay and for characterisation by SDS-PAGE and SE-HPLC. An aliquot was removed for protein assay and CA assay. The remainder was stored at 4±1° C. until further use and studied for physical stability by SE-HPLC.

The effects of various processes affecting the stability of GCSF in solution and the degree of derivatization were studied.

3.4. Pegylation of GCSF (Comparative):

GCSF (18.8 kDa) was supplied as a solution (0.5 mg/ml in 10 mM sodium acetate buffer, pH 4.0 containing 5% sorbitol, 0.025 mg/ml polysorbate 80) and stored at 2-8° C. GCSF solution was concentrated to make about 1.0 mg/ml of solution. The required amount of GCSF was taken into an eppendorf and placed on ice. The amount of PEG added for conjugation was calculated based on formula:

$$\text{Weight of } PEG = \frac{\text{Amount of protein (g)}}{\text{(MW of protein)}} \times (\text{MW of } PEG) \times (\text{Molar excess of } PEG)$$

Figure 13:
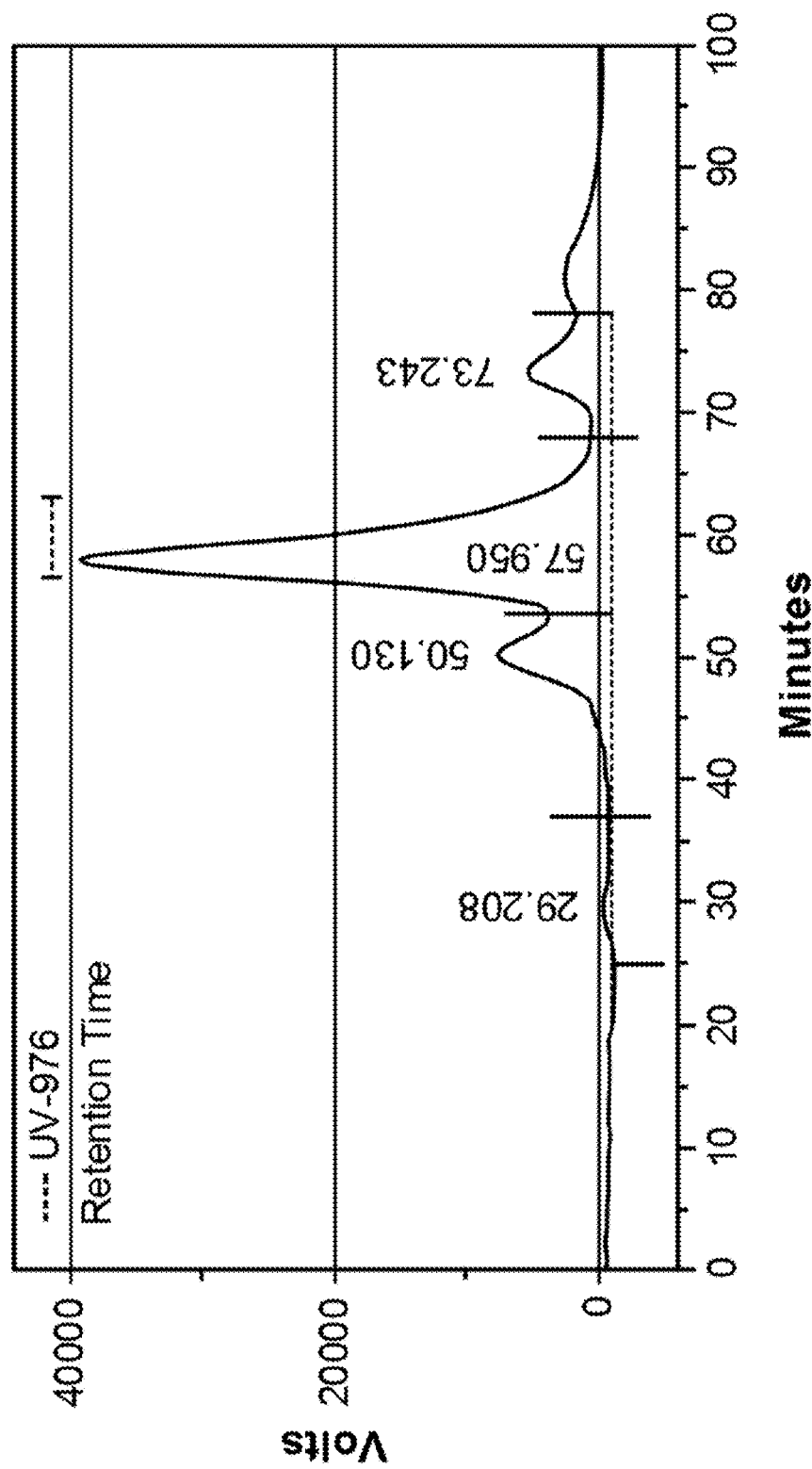
FIG. 13 shows the characterisation of pegylated GCSF by SE-HPLC.

The required amount of PEG 20K was weighed out. It was solubilized in 10 mM NaOAc. 5% sorbitol, pH 5.5 (20% volume of the final reaction volume as used here), the mixture gently vortexed until all the PEG had dissolved and then either filtered into a new eppendorf or centrifuged at 4000 rpm for 5 min and the supernatant was transferred to a new eppendorf to remove any aggregated/precipitated material. The required volume of 10 mg/ml Tween 20 stock solution was added, in order to have a final concentration of 0.5 mg/ml of the Tween 20 in the final reaction mixture. Required amount of GCSF protein solution was added to the PEG solution to give a 7.5 molar excess of PEG and gently mixed by keeping the reaction mixture on a gentle shaker at 4±1° C. 100 mg/ml NaCNBH$_3$ solution was added in order to have 50 mM or 3.17 mg/ml in the final reaction mixture, gently mixed and the pH of the final reaction mixture was checked, and if necessary adjusted to 5.5 with 1M NaOH/HCL at 4±1° C. Finally adjusted the volume of the reaction using 10 mM NaOAC, 5% sorbitol, and pH 5.5 to give a protein concentration of 1 mg/ml in the reaction mixture. The tube was sealed and stirred at desired temperature (4±1° C.) for 24 hours. The reaction was stopped by an appropriate method and samples were taken out for in vitro activity on MNSF 60 cell, SDS-PAGE (using 4-20% Tris-glycine gel), SE-HPLC (superose 6 column) and checked the pH of reaction mixture. To eliminate any precipitate the reaction mixture was centrifuged at 13000 rpm for 5 min before SE-HPLC analysis and purification, preferred buffer for SE-HPLC was 0.1 M sodium phosphate (pH 6.9). The results are shown in FIG. 13.

3.5. Metal Affinity Chromatography

Figure 8:
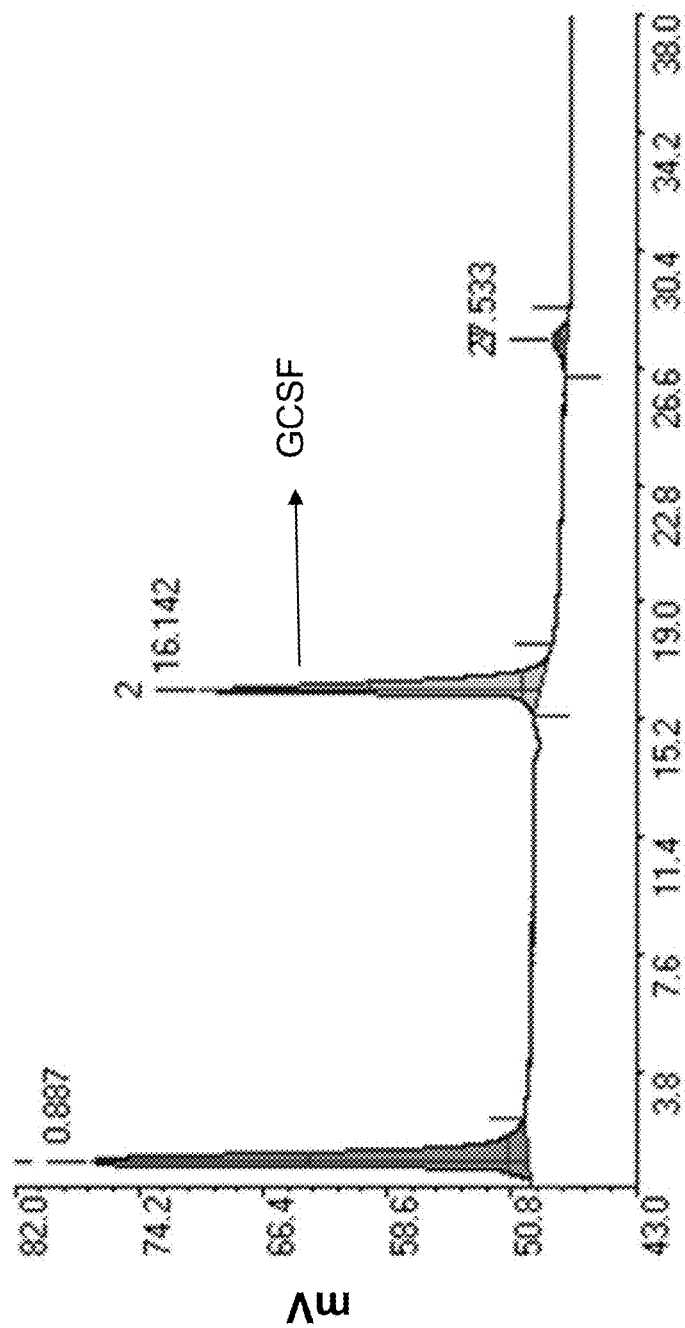
FIG. 8 illustrates the results from immobilised metal affinity chromatography of GCSF.

GCSF and PSA-GCSF conjugates were purified from the PSA and by-products of the reaction mixture by metal affinity chromatography (FIG. 8). The sample for this experiment was 50 µg GCSF in 75 µL reaction buffer+75 µl eluent A. The reaction buffer was 0.5 mg/mL Tween 20; 5% sorbitol; 10 mM NaOAc; pH 5.0. Eluent A was 10 mM Tris/HCl; pH 7.0. Eluent B was 20 mM AcOH+0.2 M NaCl; pH 4.0. Gradient: (t/min)=0 to 12.5 (100% A); t=12.5 to 25 (30% B); 25 to 40 (100% B). The peak at 0.887 is the buffer, and that at 16.142 is GCSF.

3.6. SE-HPLC of GCSF Formulations

HPLC was performed on a Liquid Chromatograph (JASCO) equipped with a Jasco, AS-2057 plus autosampler refrigerated at 4° C., and a Jasco UV-975 UV/VIS detector. Data was recorded by EZchrom Elite software on an IBM/PC. The SEC samples were analysed with an isocratic mobile phase of 0.1 M Na phosphate, pH 6.9; on a Superose 6 column (FIG. 5) in the presence of Tween. FIG. 6 shows just one peak at RT=76.408, which is attributed to GCSF.

Figure 5:
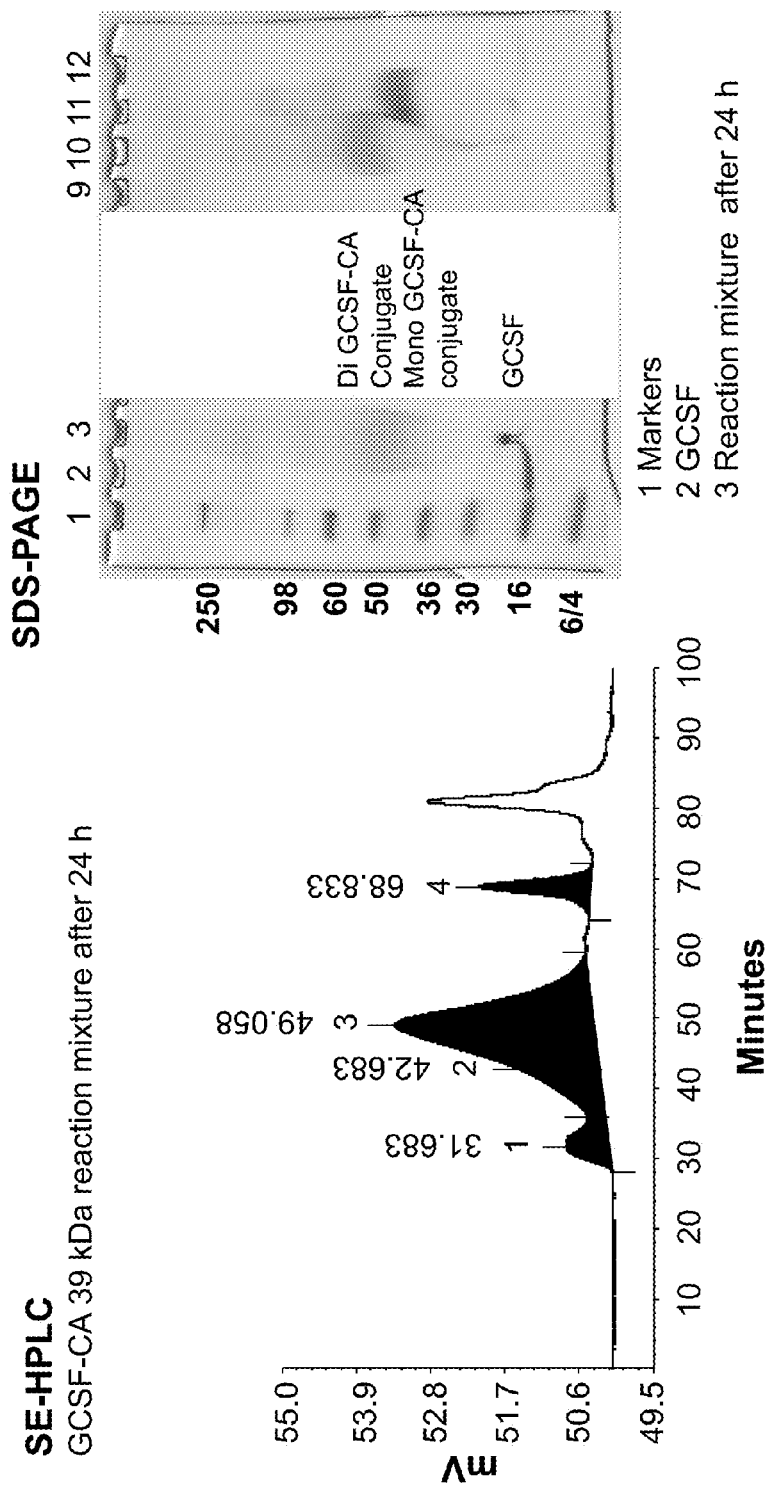
FIG. 5 shows the characterisation of SE-HPLC (left hand side) and polysialylated GCSF by SDS-PAGE (right hand side)
Figure 6:
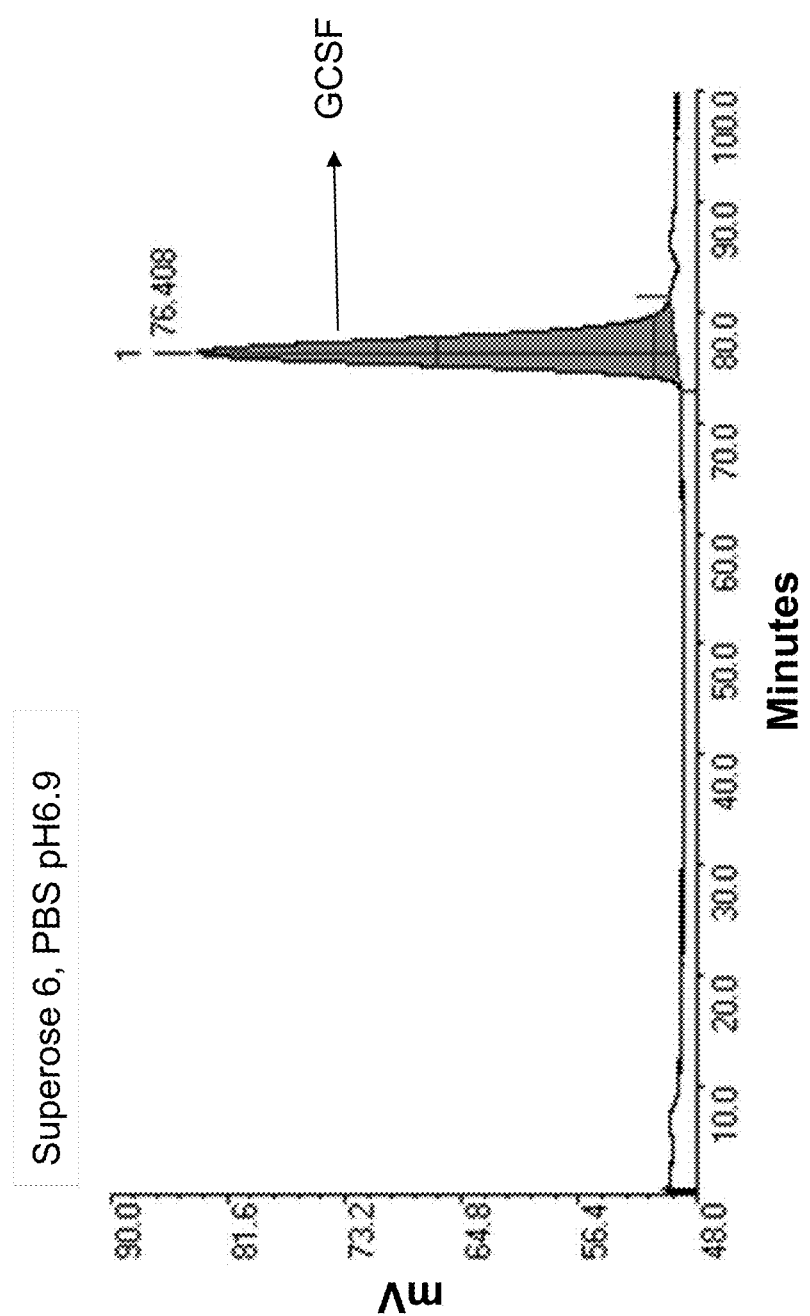
FIG. 6 shows the characterisation of GCSF by SE-HPLC.

The peak table for the SEC shown on the right hand side of FIG. 5 is as follows:

TABLE 1

| Peak | RT | % Area | Species |
|---|---|---|---|
| 1 | 33.896 | 13.9 | Aggregate |
| 2 | 60.871 | 85.7 | CA38K-GCSF |
| 3 | 76.229 | 0.4 | GCSF |

3.7. Native, SDS Polyacrylamide Gel Electrophoresis & Western Blotting

Figure 4:
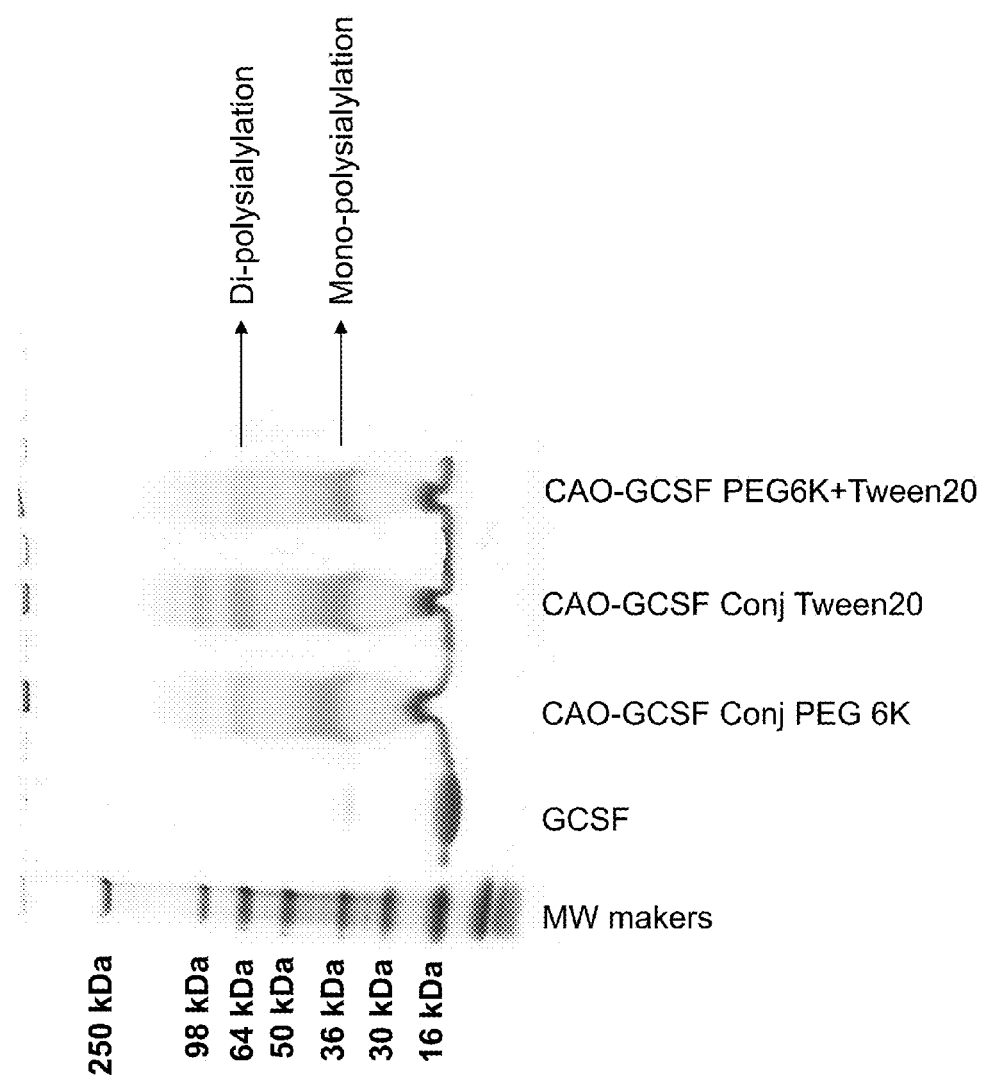
FIG. 4 shows the characterisation of polysialylated GCSF by SDS-PAGE in the presence of formulation additives.
Figure 7:
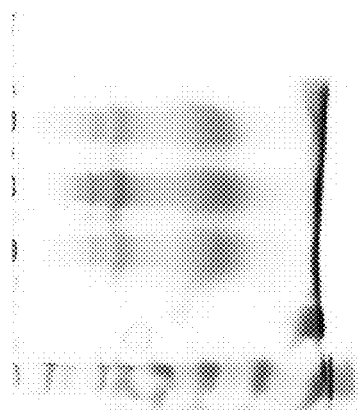
FIG. 7 shows the characterisation of polysialylated 42 kDa-GCSF by native PAGE.

SDS-PAGE was performed using 4-20% trisglycine gels. Samples were diluted with either reducing or non reducing buffer and 5.0 µg of protein was loaded into each well. The gels were run on a trisglycine buffer system and was stained with Coomassie Blue. Western blotting was performed using anti PSA antibody (FIG. 4). FIG. 4 shows the SDS-PAGE of GCSF formulations (site-specific; N-terminal). Native PAGE was performed on 10% tris glycine gel (FIG. 7).

3.8. In Vitro Activity

Figure 9:
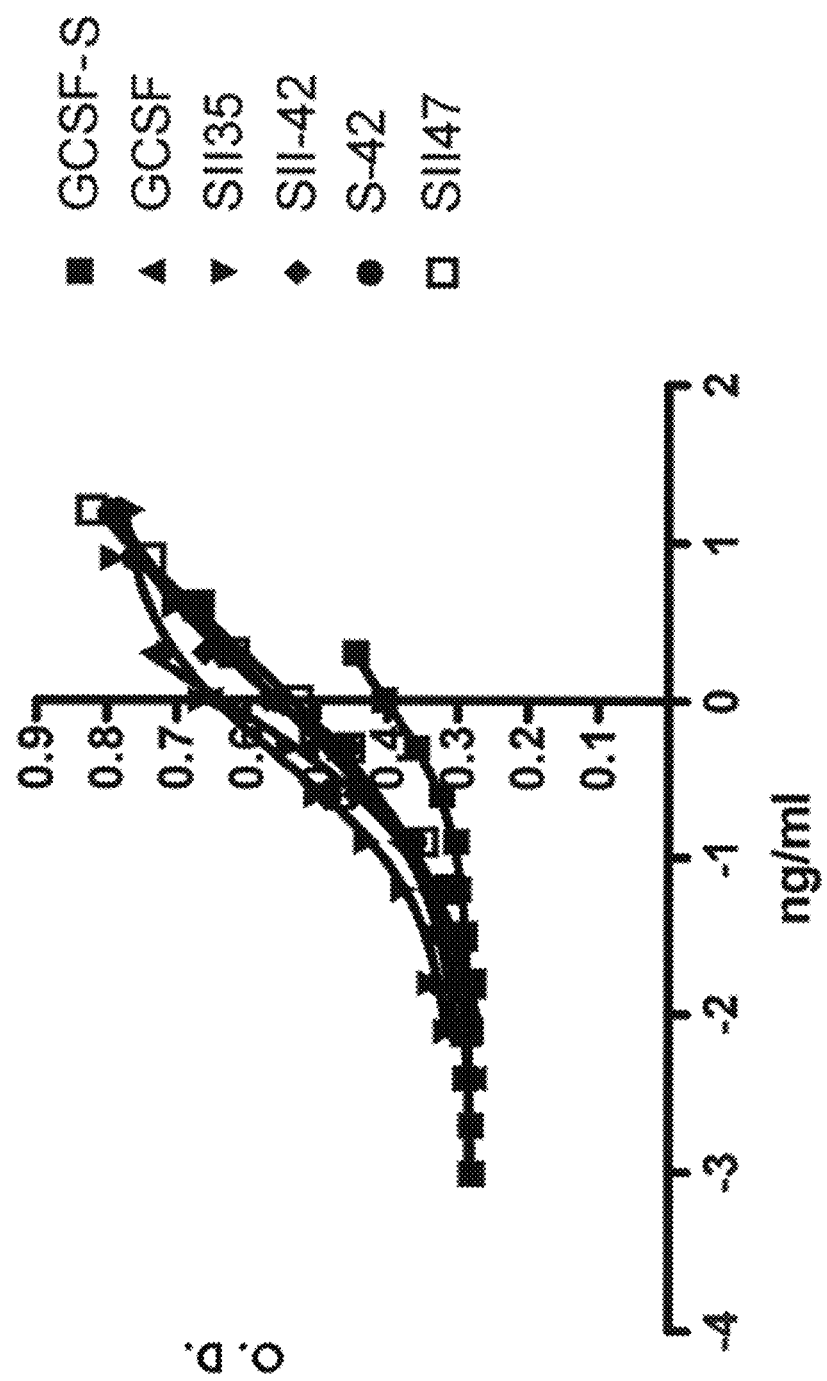
FIG. 9 illustrates the in vitro activity of polysialylated GCSF on MNFS60 cells.

In vitro studies were performed on MNFS 60 cells with GCSF, PSA and PEG conjugates. EC50 values were measured and compared for various GCSF formulations (FIG. 9).

3.9. Stability Studies

Figure 10:
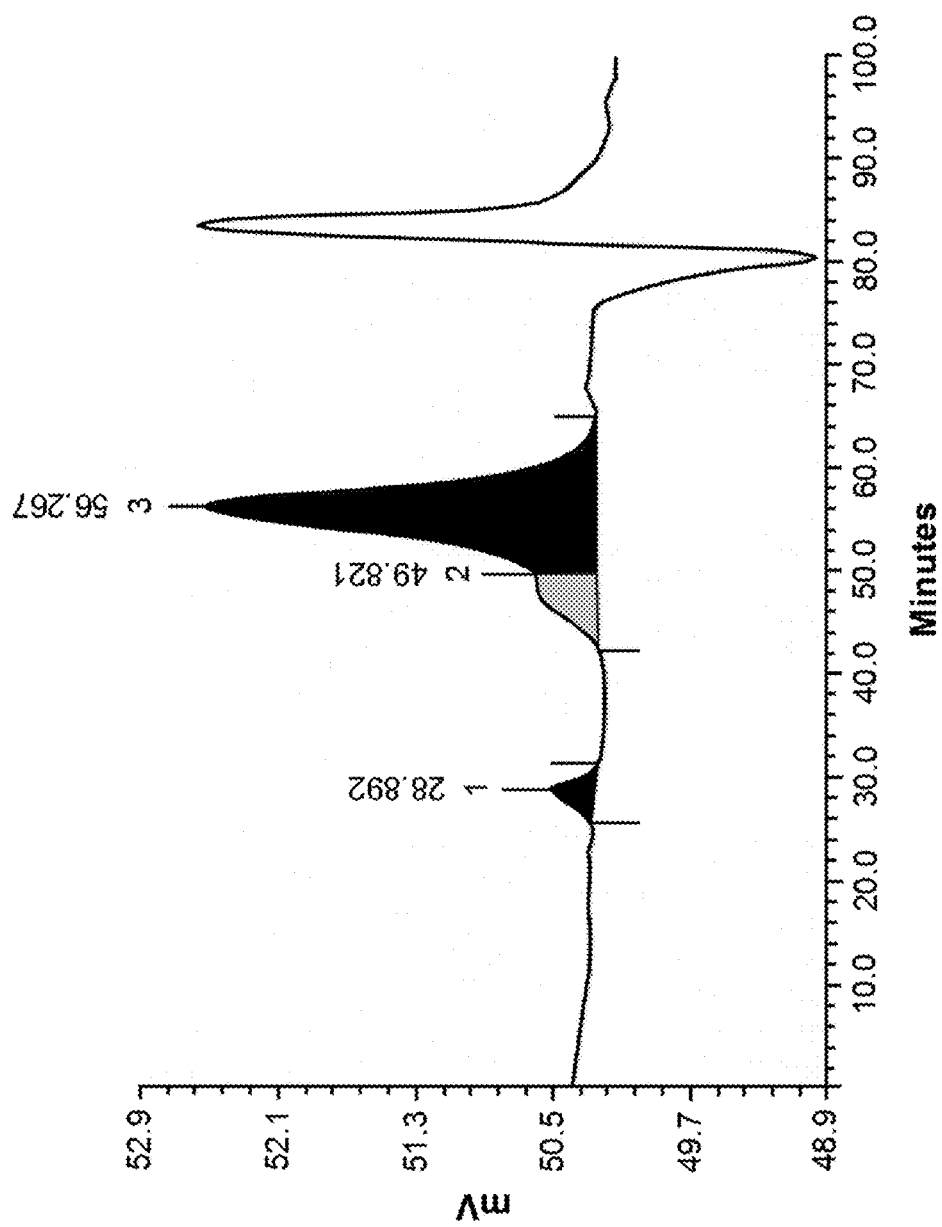
FIG. 10 shows a SE-HPLC data for the stability of polysialylated GCSF formulation (CA41 KDa-GCSF)

Sterile GCSF conjugates were stored in 20 mM sodium phosphate, pH 7.4; 5% sorbitol and 0.025 mg/ml Tween 20; at 4° C. for six weeks. SE-HPLC of the samples was performed every week using SEC columns under following conditions: Injection volume 100 µl, flow rate 0.250 ml/min, running buffer 0.1 M sodium phosphate, pH 6.9 (FIG. 10).

3.10. In Vivo Efficacy of GCSF Formulations

Figure 11:
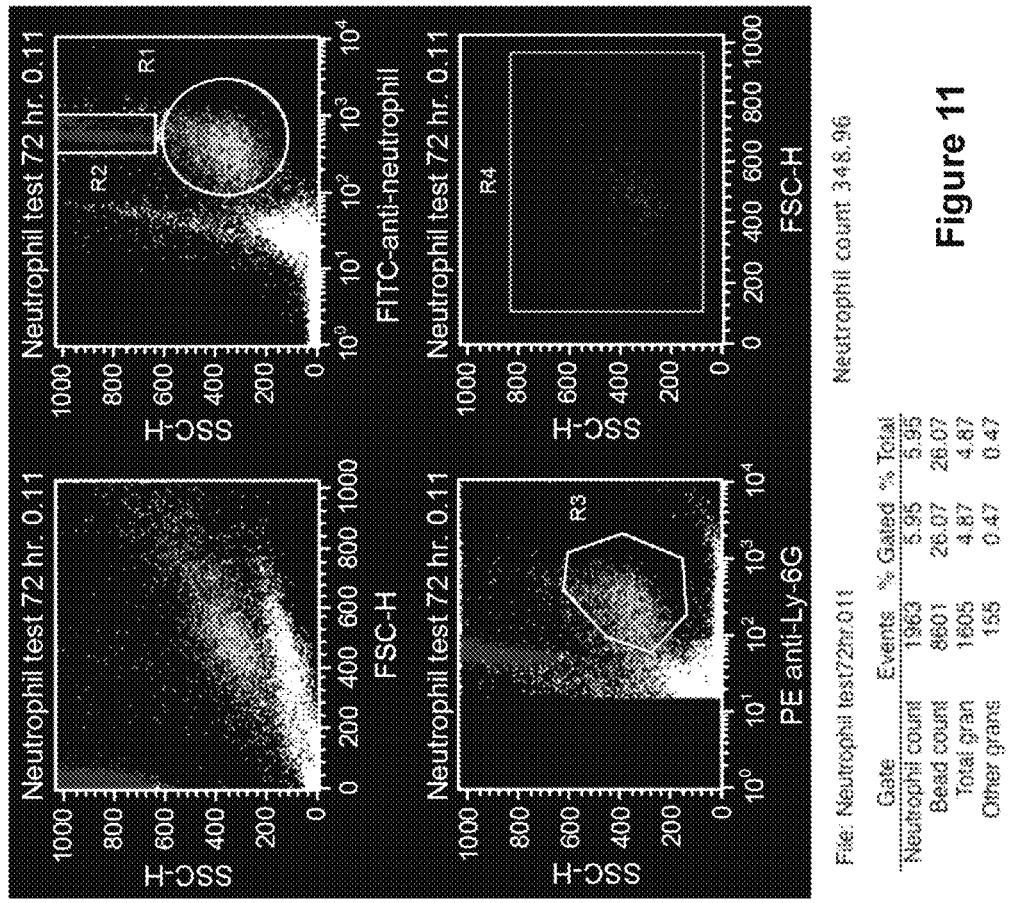
FIG. 11 shows the FACS data for GCSF (neutrophil count)
Figure 12:
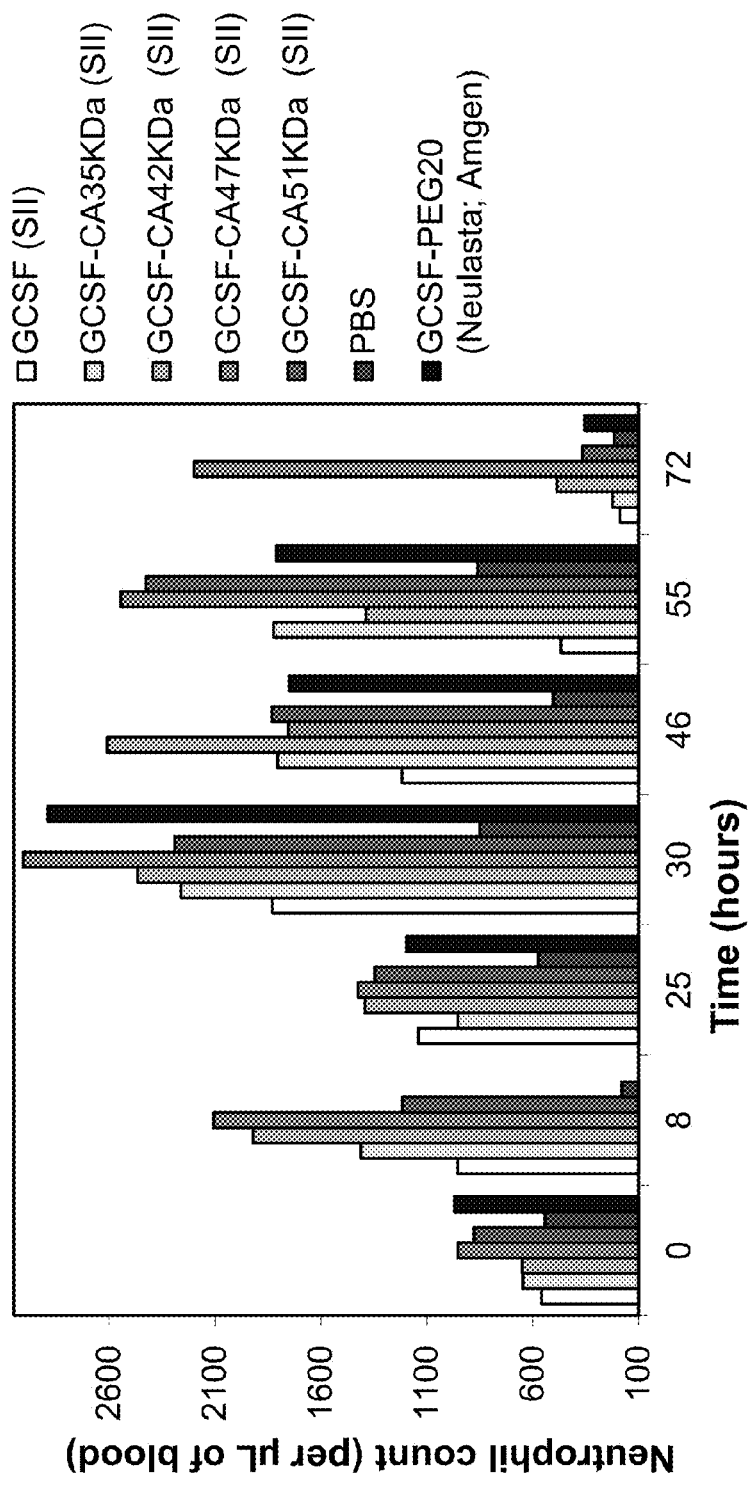
FIG. 12 shows the in vivo efficacy of GCSF formulations.

The in vivo efficacy of GCSF formulations was studied in female mice B6D2F1, 7-8 weeks old, 5-15 µgs of protein dose (same activity) was injected in mice subcutaneously. Animals were divided into seven groups of four. GCSF formulations were given to each animal of each group in the following manner; GCSF (5 µg), GCSF (15 µg), GCSF-PSA conjugates (5-15 µg), PBS, GCSF-PEG20 (NeulastaR; 5 µg). 50 µl of blood was taken from each animal and was analysed by FACS after staining with antibodies specific for WBCs (FIGS. 11 and 12).

Results

Activation of CA and Determination of Degree of Oxidation

Colominic acid (CA) is a linear alpha-2,8-linked homopolymer of N-acetylneuraminic acid (Neu5Ac) residues was used. Exposure of colominic acids to oxidation was carried out for 15 min using 20 mM periodate at room temperature. The integrity of the internal alpha-2,8 linked Neu5Ac residues post periodate treatment was analysed by gel permeation chromatography and the chromatographs obtained for the oxidised (CAO), material was compared with that of native CA. It was found that oxidized and native CA exhibit almost identical elution profiles, with no evidence that the successive oxidation step give rise to significant fragmentation of the polymer chain.

Quantitative measurement of the oxidation state of CA was performed by ferricyanide ion reduction in alkaline solution to ferrocyanide (Prussian Blue) [Park and Johnson, 1949] using glucose as a standard. Table 2 shows that the oxidized colominic acid was found to have a greater than stoichiometric (>100%) amount of reducing agent, i.e. 112 mol % of apparent aldehyde content comprising the combined reducing power of the reducing end hemiketal and the introduced aldehyde (at the other end, reducing end).

TABLE 2

Degree of oxidation of various colominic acid intermediates in the double oxidation reaction scheme using glucose as a standard (100%, 1 mole of aldehyde per mole of glucose; n = 3 ± s.d).

| CA species | Degree of oxidation |
|---|---|
| colominic acid (CA) | 16.1 ± 0.63 |
| colominic acid-oxidised (CAO) | 112.03 ± 4.97 |
| colominic acid-reduced (CAOR) | 0; Not detectable |
| colominic acid-oxidised-reduced-oxidised (CAORO) | 95.47 ± 7.11 |

Preparation, Purification and Characterisation of GCSF Conjugates

The procedure to prepare and purify colominic acid (CA) conjugates of granulocyte-colony stimulating factor (GCSF) in an N-terminally selective manner by conducting the reaction at a reduced pH (pH 5.5) and at 4±1° C. is detailed above. This involves conjugation in the presence of sodium cyanoborohydride, followed by purification using ion-exchange chromatography (AEX) to remove free GCSF followed by removal of CA by hydrophobic interaction chromatography (HIC). The low pH was used to favour selective derivatisation of the alpha amino group of the N-terminus, and also in order to minimise aggregation of GCSF during the reaction. The composition of the final reaction buffer was 5% sorbitol, 0.5 mg/ml Tween 20 in 10 mM NaOAc at pH 5.5.

Formation of the GCSF-CA conjugates and stability was confirmed by the SE-HPLC (change of retention time of GCSF-PSA as compared to GCSF; also co-elution of both moieties); ion exchange chromatography (binding of conjugates on to the AEC column) and polyacrylamide gel electrophoresis (SDS-PAGE; shifting of bands with high m.w. species and native page). The conjugates used in the in vitro cell line assay (on MNFS-60 cells) were ~40% active as compared native protein. The conjugates prepared without formulation additives led to the aggregation of protein with poor degree of derivatization. FIG. 5, shows the SE-HPLC data for GCSF-CA 39 kDa reaction mixture after 24 hours, prepared in the presence of Tween 20. The characterisation conditions were column: Superdex 200, buffer ammonium bicarbonate 0.15 M pH 7.8. The formation of GCSF-PEG conjugate was confirmed by SE-HPLC (FIG. 13). GCSF and PSA-GCSF conjugates were successfully purified from the PSA and by-products of the reaction mixture by metal affinity chromatography (FIG. 8). GCSF conjugates were found to be stable even after six weeks of storage in 20 mM sodium phosphate, pH 7.4 (FIG. 10).

Table 3 shows the peak analysis of FIG. 5.

TABLE 3

| Peak | RT | % Area | Species |
|---|---|---|---|
| 1 | 31.683 | 8.80 | aggregate |
| 2 | 42.683 | 11.77 | (CA)2-GCSF |
| 3 | 49.058 | 68.55 | CA-GCSF |
| 4 | 68.833 | 10.89 | GCSF |

Table 4 shows values of various parameters used and table 5 gives the molecular weight and polydispersity of CA fractions.

TABLE 4

| Parameters | Values |
|---|---|
| Mn (Da) | 26,666 |
| Mw (Da) | 27,956 |
| Mz (Da) | 31,129 |
| Mp (Da) | 22,969 |
| Mw/Mn | 1.048 |
| IV (dl/g) | 0.2395 |
| Rh (nm) | 4.683 |
| Branches | 0.00 |
| Sample Conc (mg/ml) | 5.600 |
| Sample Recovery (%) | 90.71 |
| dn/dc (ml/g) | 0.156 |
| dA/dc (ml/g) | 0.000 |
| Mark-Houwink a | −0.048 |
| Mark-Houwink logK | −0.425 |

TABLE 5

| CA fraction | Mw (kDa) | pd |
|---|---|---|
| 475 | 97.2 | 1.285 |
| 450 | 52.3 | 1.109 |
| 425 | 37.9 | 1.062 |
| 400 | 28.0 | 1.048 |
| 375 | 19.0 | 1.080 |
| *350 | 14.5 | — |
| *300 | 10.0 | — |
| *250 | 7.0 | — |

The PSA conjugates were found to be active in the in vitro activity assay (FIG. 9). In vivo efficacy study shows that PSA-GCSF conjugates are as good as PEG conjugates and vastly superior to GCSF (FIGS. 11 & 12).

References

Fernandes, A. I., Gregoriadis, G., Synthesis, characterization and properties of polysialylated catalase, Biochimica et Biophysica Acta, 1293 (1996) 92-96.

Fernandes, A. I., Gregoriadis, G., Polysialylated asparaginase: preparation, activity and pharmacokinetics, Biochimica et Biophysica Acta, 1341 (1997) 26-34.

Gregoriadis, G., McCormack, B., Wang, Z., Lifely, R., Polysialic acids: potential in drug delivery, FEBS Letters, 315 (1993) 271-276.

Jain et. al., Polysialylated insulin: synthesis, characterization and biological activity in vivo, Biochemica et. Biophysica Acta, 1622 (2003) 42-49.

Jain et. al., The natural way to improve the stability and pharmacokinetics of protein and peptide drugs. Drug delivery systems and sciences, 4(2), (2004) 3-9.

Park, J. T., Johnson, M. J., A submicrodetermination of glucose, Journal of Biological Chemistry, 181 (1949) 149-151.

Shriner, R. L., Fuson, R. D. C., Curtin, D. Y., Morill, T. C., The Systematic Identification of Organic Compounds, 6.sup.th ed., Wiley, New York, 1980.

Svennerholm, L., Quantitative estimation of sialic acid II: A calorimetric resorcinol-hydrochloric acid method, Biochimca et Biophysica Acta, 24 (1957) 604-611.

Wang, W., Instability, stabilization, and formulation of liquid protein pharmaceuticals, International Journal of Pharmaceutics, 185 (1999) 129-188.

The invention claimed is:

1. A composition comprising an amino-terminal polysaccharide derivative of granulocyte colony-stimulating factor (GCSF), wherein the polysaccharide is attached to the amino terminus of a protein consisting of amino acids 30-207 of SEQ ID NO: 1, or a protein having at least 95% sequence identity thereto, wherein the polysaccharide is anionic and comprises between 2 and 200 saccharide units and wherein the protein possesses at least 50% human GCSF activity as measured by a bioassay in comparison to the World Health Organization International Standard for human granulocyte colony stimulating factor (Human, rDNA-derived).

2. The composition according to claim 1, wherein the protein has at least 99% identity or similarity at the amino acid level to a protein consisting of amino acids 30-207 of SEQ ID NO: 1.

3. The composition according to claim 1, wherein the polysaccharide comprises at least 5 saccharide units.

4. The composition according to claim 1, wherein the polysaccharide comprises at least 10 saccharide units.

5. The composition according to claim 1, wherein the polysaccharide comprises at least 50 saccharide units.

6. The composition according to claim 1, wherein the polysaccharide comprises 80-180 sialic acid units.

7. The composition according to claim 1, wherein the polysaccharide comprises 100-150 sialic acid units.

8. The composition according to claim 1, wherein the polysaccharide comprises 130-140 sialic acid units.

9. The composition according to claim 1, wherein the polysaccharide consists of 130-140 sialic acid units.

* * * * *